(12) United States Patent
Suzuki et al.

(10) Patent No.: US 8,653,249 B2
(45) Date of Patent: Feb. 18, 2014

(54) EXPRESSION VECTOR FOR MASS PRODUCTION OF FOREIGN GENE-DERIVED PROTEIN USING ANIMAL CELL AND USE THEREOF

(75) Inventors: Yasuhiko Suzuki, Hokkaido (JP); Keiichi Yamamoto, Osaka (JP); Hiroshi Tahara, Osaka (JP); Yusuke Suzuki, Osaka (JP)

(73) Assignees: Fuso Pharmaceutical Industries, Ltd., Osaka (JP); National University Corporation Hokkaido University, Hokkaido (JP)

( * ) Notice: Subject to any disclaimer, the term of this patent is extended or adjusted under 35 U.S.C. 154(b) by 0 days.

(21) Appl. No.: 12/918,776

(22) PCT Filed: Feb. 27, 2009

(86) PCT No.: PCT/JP2009/053682
§ 371 (c)(1),
(2), (4) Date: Jan. 13, 2011

(87) PCT Pub. No.: WO2009/107775
PCT Pub. Date: Sep. 3, 2009

(65) Prior Publication Data
US 2011/0123993 A1 May 26, 2011

(30) Foreign Application Priority Data
Feb. 27, 2008 (JP) ................................. 2008-046782

(51) Int. Cl.
*C07H 21/04* (2006.01)
*C12Q 1/68* (2006.01)

(52) U.S. Cl.
USPC ......................................... 536/24.1; 435/6.1

(58) Field of Classification Search
None
See application file for complete search history.

(56) References Cited

U.S. PATENT DOCUMENTS

| 5,441,868 | A | 8/1995 | Lin |
| 5,760,185 | A | 6/1998 | Kimachi et al. |
| 2011/0014655 | A1* | 1/2011 | Otte et al. ................... 435/69.6 |

FOREIGN PATENT DOCUMENTS

| CN | 1771324 | 5/2006 |
| EP | 0117059 | 8/1984 |
| EP | 1 591 523 | 2/2005 |
| JP | 59-183693 | 10/1984 |
| JP | 06-30788 | 2/1994 |
| JP | 06-217786 | 8/1994 |
| JP | 07-67648 | 3/1995 |
| JP | 07-265084 | 10/1995 |
| JP | 10-179169 | 7/1998 |
| JP | 200245191 | 12/2002 |
| WO | 2004070030 | 8/2004 |
| WO | 2006/048459 | 5/2006 |

OTHER PUBLICATIONS

Bebbington; et al., "High-Level Expression of a Recombinant Antibody From Myeloma Cells Using a Glutamine Synthetase Gene as an Amplifiable Selectable Marker", Nature Biotechnology, (Feb. 1992) vol. 10, 169-175.
Gillies; et al., "High-Level expression of chimeric antibodies using adapted cDNA variable region cassettes", Journal of Immunological Methods, (Dec. 1989), 125 (1-2):191-202.
Goto; et al., "Production of Recombinant Human Erythropoietin in Mammalian Cells: Host-Cell Dependency of the Biological Activity of the Cloned Glycoprotein", Nature Biotechnology, (1988), vol. 6, 67-71.
Hud Ed; Saibo Baiyo Naruhodo Q&A, (2004), 95-6. (Question 39). (See ISR and IPRP for concise explanation).
Kim; et al, "Codon optimization for high-level expression of human erythropoietin (EPO) in mammalian cells", Gene, (Oct. 15, 1997), 199 (1-2):293-301.
Miyaji; et al., "Efficient expression of human beta-interferon in Namalwa KJM-1 cells adapted to serum-free medium by a dhfr gene coamplification method", Cytotechnology, (Sep. 1990) 4(2):173-180.
Newman;, "Primatization" of Recombinant Antibodies for Immunotherapy of Human Diseases: A Macaque/Human Chimeric Antibody Against Human CD4, (1992), vol. 10, 1455-1460.
Powell et al., "Human erythropoietin gene: High level expression in stably transfected mammalian cells and chromosome localization" Proc. Natl. Acad. Sci. USA, (Sep. 1986) 83:6465-6469.
Scahill, et al., "Expression and characterization of the product of a human immune interferon cDNA gene in Chinese hamster ovary cells", Proc. Nat. Acad. Sci. USA, (Aug. 1983), 80(15):4654-4658.
Yanagi, et al., "High-Level Expression of Human Erythropoietin cDNA in Stably Transfected Namalwa Cells", Journal of Fermentation and Bioengineering, (1989), Vol. 68, No. 4, 257-263.
International Search Report (ISR) for PCT/JP2009/063682 dated Mar. 13, 2009 from the corresponding International Application.
International Preliminary Report on Patentability (IPRP) for PCT/JP2009/063682 dated Oct. 21, 2010 from the corresponding International Application.

* cited by examiner

*Primary Examiner* — Celine X Qian
*Assistant Examiner* — Addison D Ault
(74) *Attorney, Agent, or Firm* — Karl Bozicevic; Bozicevic, Field & Francis LLP

(57) ABSTRACT

The present inventors successfully constructed expression vectors that enable high-level production of foreign gene-derived proteins in mammalian host cells, which comprise a translation-impaired drug resistance gene cistron whose expression has been attenuated by altering the codons to the least frequently used codons in mammals; and a gene cassette which has a cloning site for incorporation of a foreign gene between a highly transcriptionally active promoter and a highly stable polyadenylation signal.

8 Claims, 22 Drawing Sheets

SEQUENCE LISTING

```
<160> NUMBER OF SEQ ID NOS: 12

<210> SEQ ID NO 1
<211> LENGTH: 6078
<212> TYPE: DNA
<213> ORGANISM: Artificial
<220> FEATURE:
<223> OTHER INFORMATION: An artificially synthesized vector sequence

<400> SEQUENCE: 1
cgatgtacgg gccagatata cgcgttgaca ttgattattg actagttatt aatagtaatc      60
aattacgggg tcattagttc atagcccata tatggagttc cgcgttacat aacttacggt     120
aaatggcccg cctggctgac cgcccaacga ccccgccca ttgacgtcaa taatgacgta      180
tgttcccata gtaacgccaa tagggacttt ccattgacgt caatgggtgg agtatttacg    240
gtaaactgcc cacttggcag tacatcaagt gtatcatatg ccaagtacgc cccctattga    300
cgtcaatgac ggtaaatggc ccgcctggca ttatgcccag tacatgacct tatgggactt    360
tcctacttgg cagtacatct acgtattagt catcgctatt accatggtga tgcggttttg    420
gcagtacatc aatgggcgtg atagcggtt tgactcacgg ggatttccaa gtctccaccc     480
cattgacgtc aatgggagtt tgttttggca ccaaaatcaa cgggactttc caaaatgtcg    540
taacaactcc gccccattga cgcaaatggg cggtaggcgt gtacggtggg aggtctatat    600
aagcagagct ctctggctaa ctagagaacc cactgttaac tggcttatcg aaattgtcga    660
ggagaacttc agggtgagtt tggggaccct tgattgttct ttctttttcg ctattgtaaa    720
attcatgtta tatggagggg gcaaagtttt cagggtgttg tttagaatgg aagatgtcc     780 cttgtatcac catggaccct catgataatt ttgtttcttt cactttctac tctgttgaca    840
accattgtct cctcttattt tcttttcatt ttctgtaact ttttcgttaa actttagctt    900
gcatttgtaa cgaattttta aattcacttt tgtttatttg tcagattgta agtactttct    960
```

```
ctaatcactt tttttcaag gcaatcaggg tatattatat tgtacttcag cacagtttta    1020
gagaacaatt gttataatta aatgataagg tagaatattt ctgcatataa attctggctg    1080
gcgtggaaat attcttattg gtagaaacaa ctacatcctg gtcatcatcc tgcctttctc    1140
tttatggtta caatgatata cactgtttga gatgaggata aaatactctg agtccaaacc    1200
gggcccctct gctaaccatg ttcatgcctt cttctttttc ctacagctcc tgggcaacgt    1260
gctggcggcc gccttctaga gcctcgactg tgccttctag ttgccagcca tctgttgttt    1320
gcccctcccc cgtgccttcc ttgaccctgg aaggtgccac tcccactgtc ctttcctaat    1380
aaaatgagga aattgcatcg cattgtctga gtaggtgtca ttctattctg ggggtgggg    1440 tggggcagga cagcaagggg gaggattggg aagacaatag caggcatgct ggggaggatc    1500
tccgcggtgt ggaatgtgtg tcagttaggg tgtggaaagt ccccaggctc cccagcaggc    1560
agaagtatgc aaagcatgca tctcaattag tcagcaacca tagtcccgcc cctaactccg    1620
cccatcccgc ccctaactcc gcccagttcc gcccattctc cgccccatgg ctgactaatt    1680
ttttttattt atgcagaggc cgaggccgcc tcggcctctg agctattcca gaagtagtga    1740
ggaggctttt ttggaggcct aggcttttgc aaaaaagctg cagatgattg aacaagatgg    1800
attgcacgca ggttctccgg ccgcttgggt ggagaggcta ttcggctatg actgggcaca    1860
acagacaatc ggctgctctg atgccgccgt gttccggctg tcagcgcagg ggcgcccggt    1920
tctttttgtc aagaccgacc tgtccggtgc cctgaatgaa ctgcaggacg aggcagcgcg    1980
gctatcgtgg ctggccacga cgggcgttcc ttgcgcagct gtgctcgacg ttgtcactga    2040
agcgggaagg gactggctgc tattgggcga agtgccgggg caggatctcc tgtcatctca    2100
ccttgctcct gccgagaaag tatccatcat ggctgatgca atgcggcggc tgcatacgct    2160
tgatccggct acctgcccat tcgaccacca agcgaaacat cgcatcgagc gagcacgtac    2220
tcggatggaa gccggtcttg tcgatcagga tgatctggac gaagagcatc aggggctcgc    2280
gccagccgaa ctgttcgcca ggctcaaggc gcgcatgccc gacggcgagg atctcgtcgt    2340
gacccatggc gatgcctgct tgccgaatat catggtggaa aatggccgct tttctggatt    2400
catcgactgt ggccggctgg gtgtggcgga ccgctatcag gacatagcgt tggctacccg    2460
tgatattgct gaagagcttg gcggcgaatg ggctgaccgc ttcctcgtgc tttacggtat    2520
cgccgctccc gattcgcagc gcatcgcctt ctatcgcctt cttgacgagt tcttctgaga    2580
tccgtgacat aattggacaa actacctaca gagatttaaa gctctaaggt aaatataaaa    2640
tttttaagtg tataatgtgt taaactactg attctaattg tttgtgtatt ttagattcca    2700
acctatggaa ctgatgaatg ggagcagtgg tggaatgcct ttaatgagga aaacctgttt    2760
tgctcagaag aaatgccatc tagtgatgat gaggctactg ctgactctca acattctact    2820
cctccaaaaa agaagagaaa ggtagaagac cccaaggact tccttcaga attgctaagt    2880 tttttgagtc atgctgtgtt tagtaataga actcttgctt gctttgctat ttacaccaca    2940
aaggaaaaag ctgcactgct atacaagaaa attatgaaa aatattctgt aacctttata    3000
agtaggcata acagttataa tcataacata ctgtttttc ttactccaca caggcataga    3060
gtgtctgcta ttaataacta tgctcaaaaa ttgtgtacct ttagcttttt aatttgtaaa    3120
ggggttaata aggaatattt gatgtatagt gccttgacta gagatcataa tcagccatac    3180
cacatttgta gaggttttac ttgctttaaa aaacctccca cacctccccc tgaacctgaa    3240
acataaaatg aatgcaattg ttgttgttaa cttgtttatt gcagcttata atggttacaa    3300
ataaagcaat agcatcacaa atttcacaaa taaagcattt ttttcactgc attctagttg    3360
```

```
tggtttgtcc aaactcatca atgtatctta tcatgtctgg gcccatcgat gaattcaacg   3420
tacgtagctt ggcactggcc gtcgttttac aacgtcgtga ctgggaaaac cctggcgtta   3480
cccaacttaa tcgccttgca gcacatcccc ctttcgccag ctggcgtaat agcgaagagg   3540
cccgcaccga tcgcccttcc caacagttgc gcagcctgaa tggcgaatgg cgcctgatgc   3600
ggtattttct ccttacgcat ctgtgcggta tttcacaccg catatggtgc actctcagta   3660
caatctgctc tgatgccgca tagttaagcc agccccgaca cccgccaaca cccgctgacg   3720
cgccctgacg ggcttgtctg ctcccggcat ccgcttacag acaagctgtg accgtctccg   3780
ggagctgcat gtgtcagagg ttttcaccgt catcaccgaa acgcgcgagg acgaaagggc   3840
ctcgtgatac gcctattttt ataggttaat gtcatgataa taatggtttc ttagacgtca   3900
ggtggcactt ttcggggaaa tgtgcgcgga acccctattt gtttattttt ctaaatacat   3960
tcaaatatgt atccgctcat gagacaataa ccctgataaa tgcttcaata atattgaaaa   4020
aggaagagta tgagtattca acatttccgt gtcgccctta ttccctttttt gcggcattt   4080 tgccttcctg tttttgctca cccagaaacg ctggtgaaag taaaagatgc tgaagatcag   4140
ttgggtgcac gagtgggtta catcgaactg gatctcaaca gcggtaagat ccttgagagt   4200
tttcgccccg aagaacgttt tccaatgatg agcacttttta aagttctgct atgtggcgcg   4260
gtattatccc gtattgacgc cgggcaagag caactcggtc gccgcataca ctattctcag   4320
aatgacttgg ttgagtactc accagtcaca gaaaagcatc ttacggatgg catgacagta   4380
agagaattat gcagtgctgc cataaccatg agtgataaca ctgcggccaa cttacttctg   4440
acaacgatcg gaggaccgaa ggagctaacc gcttttttgc acaacatggg ggatcatgta   4500
actcgccttg atcgttggga accggagctg aatgaagcca taccaaacga cgagcgtgac   4560
accacgatgc ctgtagcaat ggcaacaacg ttgcgcaaac tattaactgg cgaactactt   4620
actctagctt cccggcaaca attaatagac tggatggagg cggataaagt tgcaggacca   4680
cttctgcgct cggcccttcc ggctggctgg tttattgctg ataaatctgg agccggtgag   4740
cgtgggtctc gcggtatcat tgcagcactg gggccagatg gtaagccctc ccgtatcgta   4800
gttatctaca cgacggggag tcaggcaact atggatgaac gaaatagaca gatcgctgag   4860
ataggtgcct cactgattaa gcattggtaa ctgtcagacc aagtttactc atatatactt   4920
tagattgatt taaaacttca ttttttaattt aaaaggatct aggtgaagat cctttttgat   4980
aatctcatga ccaaaatccc ttaacgtgag ttttcgttcc actgagcgtc agaccccgta   5040
gaaaagatca aaggatcttc ttgagatcct ttttttctgc gcgtaatctg ctgcttgcaa   5100
acaaaaaaac caccgctacc agcggtggtt tgtttgccgg atcaagagct accaactctt   5160
tttccgaagg taactggctt cagcagagcg cagataccaa atactgtcct tctagtgtag   5220
ccgtagttag gccaccactt caagaactct gtagcaccgc ctacatacct cgctctgcta   5280
atcctgttac cagtggctgc tgccagtggc gataagtcgt gtcttaccgg gttggactca   5340
agacgatagt taccggataa ggcgcagcgg tcggctgaa cggggggttc gtgcacacag   5400
cccagcttgg agcgaacgac ctacaccgaa ctgagatacc tacagcgtga gcattgagaa   5460
agcgccacgc ttcccgaagg gagaaaggcg gacaggtatc cggtaagcgg cagggtcgga   5520
acaggagagc gcacgaggga gcttccaggg ggaaacgcct ggtatcttta tagtcctgtc   5580
gggtttcgcc acctctgact tgagcgtcga ttttgtgat gctcgtcagg ggggcggagc   5640
ctatggaaaa acgccagcaa cgcggccttt ttacggttcc tggccttttg ctggcctttt   5700
gctcacatgt tctttcctgc gttatcccct gattctgtgg ataaccgtat taccgccttt   5760
```

```
gagtgagctg ataccgctcg ccgcagccga acgaccgagc gcagcgagtc agtgagcgag      5820
gaagcggaag agcgcccaat acgcaaaccg cctctccccg cgcgttggcc gattcattaa      5880
tgcagctggc acgacaggtt tcccgactgg aaagcgggca gtgagcgcaa cgcaattaat      5940
gtgagttagc tcactcatta ggaccccag gctttacact ttatgcttcc ggctcgtatg       6000
ttgtgtggaa ttgtgagcgg ataacaattt cacacaggaa acagctatga ccatgattac      6060
gaatttcgta cgaagctt                                                     6078

<210> SEQ ID NO 2
<211> LENGTH: 795
<212> TYPE: DNA
<213> ORGANISM: Artificial
<220> FEATURE:
<223> OTHER INFORMATION: An artificially synthesized nucleotide sequence

<400> SEQUENCE: 2
atgattgaac aagatggttt acatgcaggt tcaccagcag catgggtaga acgattattt        60
ggttatgatt gggcacaaca aactattggt tgttcagatg cagcagtatt tcgattatca      120
gcacaaggtc gaccagtatt atttgtaaaa actgatttat caggtgcatt aaatgaatta      180
caagatgaag cagcacgatt atcatggtta gcaactactg gtgtaccatg tgcagcagta      240
ttagatgtag taactgaagc aggtcgagat tggttattat taggtgaagt accaggtcaa      300
gatttattat catcacattt agcaccagca gaaaaagtat caattatggc agatgcaatg      360
cgacgattac atactttaga tccagcaact tgtccatttg atcatcaagc aaaacatcga      420
attgaacgag cacgaactcg aatggaagca ggtttagtag atcaagatga tttagatgaa      480
gaacatcaag gttagcacc agcagaatta tttgcacgat aaaagcacg aatgccagat       540 ggtgaagatt tagtagtaac tcatggtgat gcatgtttac caaatattat ggtagaaaat      600
ggtcgatttt caggttttat tgattgtggt cgattaggtg tagcagatcg atatcaagat      660
attgcattag caactcgaga tattgcagaa gaattaggtg gtgaatgggc agatcgatttt     720 ttagtattat atggtattgc agcaccagat tcacaacgaa ttgcatttta tcgattatta      780
gatgaatttt tttga                                                       795

<210> SEQ ID NO 3
<211> LENGTH: 795
<212> TYPE: DNA
<213> ORGANISM: Artificial
<220> FEATURE:
<223> OTHER INFORMATION: An artificially synthesized nucleotide sequence

<400> SEQUENCE: 3
atgattgaac aagatggttt acatgcaggt tcaccagcag catgggtaga acgattattt        60
ggttatgatt gggcacaaca aactattggt tgctctgatg ccgccgtgtt ccggctgtca      120
gcgcaggggc gcccggttct ttttgtcaag accgacctgt ccggtgccct gaatgaactg      180
caggacgagg cagcgcggct atcgtggctg gccacgacgg gcgttccttg cgcagctgtg      240
ctcgacgttg tcactgaagc gggaagggac tggctgctat tgggcgaagt gccggggcag      300
gatctcctgt catctcacct tgctcctgcc gagaaagtat ccatcatggc tgatgcaatg      360
cggcggctgc atacgcttga tccggctacc tgcccattcg accaccaagc gaaacatcgc      420
atcgagcgag cacgtactcg gatggaagcc ggtcttgtcg atcaggatga tctggacgaa      480
gagcatcagg ggctcgcgcc agccgaactg ttcgccaggc tcaaggcgcg catgcccgac      540
ggcgaggatc tcgtcgtgac ccatggcgat gcctgcttgc cgaatatcat ggtggaaaat      600
```

```
ggccgctttt ctggattcat cgactgtggc cggctgggtg tggcggaccg ctatcaggac    660
atagcgttgg ctaccgtga tattgctgaa gagcttggcg gcgaatgggc tgaccgcttc    720
ctcgtgcttt acggtatcgc cgctcccgat tcgcagcgca tcgccttcta tcgccttctt    780
gacgagttct tctga                                                    795

<210> SEQ ID NO 4
<211> LENGTH: 795
<212> TYPE: DNA
<213> ORGANISM: Artificial
<220> FEATURE:
<223> OTHER INFORMATION: An artificially synthesized nucleotide sequence

<400> SEQUENCE: 4
atgattgaac aagatggttt acatgcaggt tcaccagcag catgggtaga acgattattt     60
ggttatgatt gggcacaaca aactattggt tgttcagatg cagcagtatt tcgattatca    120
gcacaaggtc gaccagtatt atttgtaaaa actgatttat caggtgcatt aaatgaatta    180
caggacgagg cagcgcggct atcgtggctg gccacgacgg gcgttccttg cgcagctgtg    240
ctcgacgttg tcactgaagc gggaagggac tggctgctat gggcgaagt gccggggcag    300 gatctcctgt catctcacct tgctcctgcc gagaaagtat ccatcatggc tgatgcaatg    360
cggcggctgc atacgcttga tccggctacc tgcccattcg accaccaagc gaaacatcgc    420
atcgagcgag cacgtactcg gatggaagcc ggtcttgtcg atcaggatga tctggacgaa    480
gagcatcagg ggctcgcgcc agccgaactg ttcgccaggc tcaaggcgcg catgcccgac    540
ggcgaggatc tcgtcgtgac ccatggcgat gcctgcttgc cgaatatcat ggtggaaaat    600
ggccgctttt ctggattcat cgactgtggc cggctgggtg tggcggaccg ctatcaggac    660
atagcgttgg ctaccgtga tattgctgaa gagcttggcg gcgaatgggc tgaccgcttc    720
ctcgtgcttt acggtatcgc cgctcccgat tcgcagcgca tcgccttcta tcgccttctt    780
gacgagttct tctga                                                    795

<210> SEQ ID NO 5
<211> LENGTH: 795
<212> TYPE: DNA
<213> ORGANISM: Artificial
<220> FEATURE:
<223> OTHER INFORMATION: An artificially synthesized nucleotide sequence

<400> SEQUENCE: 5
atgattgaac aagatggttt acatgcaggt tcaccagcag catgggtaga acgattattt     60
ggttatgatt gggcacaaca aactattggt tgttcagatg cagcagtatt tcgattatca    120
gcacaaggtc gaccagtatt atttgtaaaa actgatttat caggtgcatt aaatgaatta    180
caagatgaag cagcacgatt atcatggtta gcaactactg gtgtaccatg tgcagcagta    240
ttagatgtag taactgaagc aggtcgagat tggctgctat gggcgaagt gccggggcag    300 gatctcctgt catctcacct tgctcctgcc gagaaagtat ccatcatggc tgatgcaatg    360
cggcggctgc atacgcttga tccggctacc tgcccattcg accaccaagc gaaacatcgc    420
atcgagcgag cacgtactcg gatggaagcc ggtcttgtcg atcaggatga tctggacgaa    480
gagcatcagg ggctcgcgcc agccgaactg ttcgccaggc tcaaggcgcg catgcccgac    540
ggcgaggatc tcgtcgtgac ccatggcgat gcctgcttgc cgaatatcat ggtggaaaat    600
ggccgctttt ctggattcat cgactgtggc cggctgggtg tggcggaccg ctatcaggac    660
atagcgttgg ctaccgtga tattgctgaa gagcttggcg gcgaatgggc tgaccgcttc    720
```

```
ctcgtgcttt acggtatcgc cgctcccgat tcgcagcgca tcgccttcta tcgccttctt    780
gacgagttct tctga                                                    795

<210> SEQ ID NO 6
<211> LENGTH: 759
<212> TYPE: DNA
<213> ORGANISM: Homo sapiens

<400> SEQUENCE: 6
ggccgccacc atgagcctgt tccccagcct gccctgctg ctgctgagca tggtggccgc      60
cagctacagc gagaccgtga cctgcgagga cgcccagaag acctgccccg ccgtgattgc    120
ctgcagcagc cccggcatca acggcttccc cggcaaggac ggccgcgacg gcaccaaggg    180
cgagaagggc gagcccggcc agggcctgcg cggcctgcag ggccccccg gcaagctggg    240 cccccccggc aaccccggcc ccagcggcag ccccggcccc aagggccaga agggcgaccc    300
cggcaagagc cccgacggcg acagcagcct ggccgccagc gagcgcaagg ccctgcagac    360
cgagatggcc cgcatcaaga agtggctgac cttcagcctg ggcaagcagg tgggcaacaa    420
gttcttcctg accaacggcg agataatgac cttcgagaag gtgaaggccc tgtgcgtgaa    480
gttccaggcc agcgtggcca ccccccgcaa cgccgccgag aacggcgcca ttcagaacct    540
gatcaaggag gaggccttcc tgggcatcac cgacgagaag accgagggcc agttcgtgga    600
cctgaccggc aaccgcctga cctacaccaa ctggaacgag ggcgagccca caacgccgg    660 cagcgacgag gactgcgtgc tgctgctgaa gaacggccag tggaacgacg tgccctgcag    720
caccagccac ctggccgtgt gcgagttccc catctgaat                          759

<210> SEQ ID NO 7
<211> LENGTH: 375
<212> TYPE: DNA
<213> ORGANISM: Artificial
<220> FEATURE:
<223> OTHER INFORMATION: An artificially synthesized nucleotide sequence

<400> SEQUENCE: 7
atggccaagt tgaccagtgc cgttccggtg ctcaccgcgc gcgacgtcgc cggagcggtc      60
gagttctgga ccgaccggct cgggttctcc cgggacttcg tggaggacga cttcgccggt    120
gtggtccggg acgacgtgac cctgttcatc agcgcggtcc aggaccaggt ggtgccggac    180
aacaccctgg cctgggtgtg tgtgcgcggc ctggacgagc tgtacgccga gtggtcggag    240
gtcgtgtcca cgaacttccg ggacgcctcc gggccggcca tgaccgagat cggcgagcag    300
ccgtggggcc gggagttcgc cctgcgcgac ccggccggca actgcgtgca cttcgtggcc    360
gaggagcagg actga                                                    375

<210> SEQ ID NO 8
<211> LENGTH: 375
<212> TYPE: DNA
<213> ORGANISM: Artificial
<220> FEATURE:
<223> OTHER INFORMATION: An artificially synthesized nucleotide sequence

<400> SEQUENCE: 8
atggcaaaat taacttcagc agtaccagta ttaactgcac gagatgtagc aggtgcagta      60 gaatttttgga ctgatcgatt aggttttttca cgagattttg tagaagatga ttttgcaggt    120
gtagtacgag atgatgtaac tttatttatt tcagcagtac aagatcaagt agtaccagat    180
aatactttag catgggtatg tgtacgaggt ttagatgaat tatatgcaga atggtcagaa    240
```

```
gtagtatcaa ctaattttcg agatgcatca ggtccagcaa tgactgaaat tggtgaacaa      300
ccatggggtc gagaatttgc attacgagat ccagcaggta attgtgtaca ttttgtagca      360
gaagaacaag attga                                                       375
```

```
<210> SEQ ID NO 9
<211> LENGTH: 375
<212> TYPE: DNA
<213> ORGANISM: Artificial
<220> FEATURE:
<223> OTHER INFORMATION: An artificially synthesized nucleotide sequence

<400> SEQUENCE: 9
atggcaaaat taacttcagc agtaccagta ttaactgcac gagatgtagc aggtgcagta       60
gaattttgga ctgatcgatt aggttttttca cgggacttcg tggaggacga cttcgccggt     120
gtggtccggg acgacgtgac cctgttcatc agcgcggtcc aggaccaggt ggtgccggac     180
aacaccctgg cctgggtgtg tgtgcgcggc ctggacgagc tgtacgccga gtggtcggag     240
gtcgtgtcca cgaacttccg ggacgcctcc gggccggcca tgaccgagat cggcgagcag     300
ccgtgggggc gggagttcgc cctgcgcgac ccggccggca ctgcgtgca cttcgtggcc      360 gaggagcagg actga                                                       375
```

```
<210> SEQ ID NO 10
<211> LENGTH: 375
<212> TYPE: DNA
<213> ORGANISM: Artificial
<220> FEATURE:
<223> OTHER INFORMATION: An artificially synthesized nucleotide sequence

<400> SEQUENCE: 10
atggcaaaat taacttcagc agtaccagta ttaactgcac gagatgtagc aggtgcagta       60
gaattttgga ctgatcgatt aggttttttca cgagattttg tagaagatga ttttgcaggt     120
gtagtacgag atgatgtaac tttatttatt tcagcagtac aagatcaagt agtaccagat     180
aacaccctgg cctgggtgtg tgtgcgcggc ctggacgagc tgtacgccga gtggtcggag     240
gtcgtgtcca cgaacttccg ggacgcctcc gggccggcca tgaccgagat cggcgagcag     300
ccgtgggggc gggagttcgc cctgcgcgac ccggccggca ctgcgtgca cttcgtggcc      360 gaggagcagg actga                                                       375
```

```
<210> SEQ ID NO 11
<211> LENGTH: 393
<212> TYPE: DNA
<213> ORGANISM: Artificial
<220> FEATURE:
<223> OTHER INFORMATION: An artificially synthesized nucleotide sequence

<400> SEQUENCE: 11
atgcctttgt ctcaagaaga atccaccctc attgaaagag caacggctac aatcaacagc       60
atccccatct ctgaagacta cagcgtcgcc agcgcagctc tctctagcga cggccgcatc      120
ttcactggtg tcaatgtata tcattttact ggggacctt gtgcagaact cgtggtgctg      180
ggcactgctg ctgctgcggc agctggcaac ctgacttgta tcgtcgcgat cggaaatgag     240 aacagggca tcttgagccc ctgcggacgg tgtcgacagg tgcttctcga tctgcatcct      300
gggatcaaag cgatagtgaa ggacagtgat ggacagccga cggcagttgg gattcgtgaa     360
ttgctgccct ctggttatgt gtgggagggc taa                                  393
```

```
<210> SEQ ID NO 12
<211> LENGTH: 399
<212> TYPE: DNA
<213> ORGANISM: Artificial
<220> FEATURE:
<223> OTHER INFORMATION: An artificially synthesized nucleotide sequence

<400> SEQUENCE: 12
atggcaaaac cattatcaca agaagaatca actttaattg aacgagcaac tgcaactatt        60
aattcaattc caatttcaga agattattca gtagcatcag cagcattatc atcagatggt       120
cgcatcttca ctggtgtcaa tgtatatcat tttactgggg gaccttgtgc agaactcgtg       180
gtgctgggca ctgctgctgc tgcggcagct ggcaacctga cttgtatcgt cgcgatcgga       240
aatgagaaca ggggcatctt gagccctgc ggacggtgcc gacaggtgct tctcgatctg        300
catcctggga tcaaagccat agtgaaggac agtgatggac agccgacggc agttgggatt       360
cgtgaattgc tgccctctgg ttatgtgtgg gagggctaa                              399
```

EXPRESSION VECTOR FOR MASS PRODUCTION OF FOREIGN GENE-DERIVED PROTEIN USING ANIMAL CELL AND USE THEREOF

TECHNICAL FIELD

The present invention relates to mammalian cell expression vectors that confer mammalian host cells with the ability of producing high levels of foreign gene-derived proteins. The expression vectors of the present invention are particularly suitable for production of mammalian proteins which require glycosylation and folding unique to mammals and hardly have sufficient activity when produced by genetic recombination using E. coli or yeast as host.

BACKGROUND ART

A large number of vectors for producing recombinant proteins have been developed, and the expression levels of proteins are high in expression systems that use bacteria such as E. coli, eukaryotic microorganisms such as yeast, and insect cells as host. However, when expressing proteins unique to mammals, they may not form a normal three-dimensional structure, and most of the time there is a problem with post-translational modifications such as glycosylation. Thus, it is necessary to establish expression systems that use mammalian cells as host, but in general, the expression level is low in most cases. Furthermore, expression systems that use recombinant virus vectors are also used in animal cells, which are higher than insect cells, but removing recombinant virus vectors from the expressed proteins is a very cumbersome process and the risk of virus vectors themselves cannot be denied.

Cases of recombinant protein production using a mammalian cell as host include tissue plasminogen activator (Patent Document 1), erythropoietin (Patent Document 2 and Non-patent Documents 1-3), IFN-γ (Non-patent Document 4), and IFN-β (Patent Document 3 and Non-patent Document 5). Furthermore, there are many reports about recombinant production of monoclonal antibodies (Patent Documents 4 to 6, and Non-patent Documents 6 to 8). In addition, an example of a high expression vector for mammalian cells is pNOW/CMV-AA (Patent Document 7). The production level of conglutinin using this vector was up to 11.8 μg/mL after four days of culture. However, the production level of recombinant protein is unlikely to be sufficient in these cases.

Prior art documents relating to the invention of this application are shown below.
[Patent Document 1] Japanese Patent Application Kokai Publication No. (JP-A) S59-183693 (unexamined, published Japanese patent application)
[Patent Document 2] JP-A (Kokai) 2002-45191
[Patent Document 3] JP-A (Kokai) H07-265084
[Patent Document 4] JP-A (Kokai) H07-67648
[Patent Document 5] JP-A (Kokai) H06-30788
[Patent Document 6] JP-A (Kokai) H06-217786
[Patent Document 7] JP-A (Kokai) H10-179169
[Non-patent Document 1] Fermentation Bioengineering, (1989) 4: p. 257
[Non-patent Document 2] Proc. Natl. Acad. Sci. USA, (1986) 83: p. 6465
[Non-patent Document 3] Biotechnology, (1988) 6: p. 67
[Non-patent Document 4] Proc. Natl. Acad. Sci. USA, (1983) 80: p. 4564
[Non-patent Document 5] Cytotechnology, (1990) 4: p. 173
[Non-patent Document 6] Biotechnology, (1992) 10: p. 169
[Non-patent Document 7] J. Immunol. Methods, (1989) 125: p. 191
[Non-patent Document 8] Biotechnology, (1992) 10: p. 1455

DISCLOSURE OF THE INVENTION

Problems to be Solved by the Invention

Use of mammalian cells, particularly Chinese hamster ovary cells (hereinafter, CHO cells) in production of pharmaceutical agents, has been confirmed safe and becomes a common technique now. In the production of recombinant proteins using mammalian cells, increasing the productivity is very important from the aspects of cost reduction, healthcare cost containment, and such. Therefore, development of expression vectors for producing transformants having a high-level production ability through efficient gene transfer is necessary.

Efficient gene transfer is necessary for easy production of high levels of recombinant protein in mammalian cells. Efficient gene transfer means that the probability of obtaining clones with high-level productivity is high regardless of whether clone selection is easy or not. Specifically, this means that the number of viable cell clones to all transformed cells after drug selection is relatively small, and therefore selection of clones with high-level productivity is easy. It also means that the probability of occurrence of clones with high-level productivity is high even if the number of cells producing the protein of interest is small. As the number of available cells becomes large, more time and effort are required for selection, and leads to inefficiency and high probability of overlooking clones that potentially have high-level production ability.

High-level production ability refers to high expression level of recombinant protein in the transformed cell clones obtained by gene transfer, and this is considered to be mainly due to the characteristics and performance of the expression vectors. It has been found that the level of gene expression is remarkably different depending on the chromosomal position (Annu. Rev. Cell Biol., 6, page 679, 1990), and introduction of a gene of interest to a region with high transcriptional activity on the chromosome (hereinafter, transcriptional hot spot) is likely to increase the level of recombinant protein production.

The present invention was achieved in view of the above circumstances. An objective of the present invention is to provide expression vectors for mammalian cells which confer mammalian host cells with the ability of producing foreign gene-derived proteins at high levels. Another objective of the present invention is to provide methods for producing transformants utilizing the above-mentioned vectors and methods for producing foreign gene-derived proteins utilizing the above-mentioned vectors.

Means for Solving the Problems

As a result of dedicated investigation to solve the above-mentioned problems, the present inventors have successfully developed expression vectors carrying a mechanism in which plasmid DNA is integrated into the transcriptional hot spot on the host cell chromosome, and cells are selected as strains resistant to a drug (for example, neomycin, Zeocin, or blasticidin). High productivity of the primary clones of transduced G418-resistant strains is dependent on the NPT gene expression mechanism, high productivity of the primary clones of Zeocin-resistant strains is dependent on the Zeocin-resistant gene expression mechanism, and high productivity of the primary clones of blasticidin-resistant strains is dependent on the blasticidin-resistant gene expression mechanism. As a result, the present inventors completed the present invention by constructing expression vectors that enable high-level, stable protein production.

More specifically, the present invention provides the following:

[1] an expression vector that enables high-level production of a foreign gene-derived protein in a mammalian host cell, which comprises:
(a) a translation-impaired drug resistance gene cassette, whose expression is attenuated by altering codons to the least frequently used codons in a mammal; and
(b) a gene cassette comprising a cloning site for integration of a foreign gene between a highly transcriptionally active promoter and a highly stable polyadenylation signal;
[2] the expression vector of [1], wherein the codons of the translation-impaired drug resistance gene cassette of [1](a) have been altered to the least frequently used codons in humans;
[3] the expression vector of [1], wherein the codons of the translation-impaired drug resistance gene cassette of [1](a) have been altered to GCA for alanine, CGA for arginine, AAU for asparagine, GAU for aspartic acid, UGU for cysteine, CAA for glutamine, GAA for glutamic acid, GGU for glycine, CAU for histidine, UUA for leucine, AAA for lysine, CCA for proline, UUU for phenylalanine, UCA for serine, ACU for threonine, UAU for tyrosine, and/or GUA for valine;
[4] the expression vector of [1], wherein the translation-impaired drug resistance gene cassette of [1](a) uses a promoter with low expression-inducing activity as the promoter;
[5] the expression vector of [4], wherein the low-activity promoter used is a promoter derived from a gene that is hardly expressed in a mammalian cell or a promoter whose enhancer portion has been removed;
[6] the expression vector of [1], wherein a codon-altered region in the translation-impaired drug resistance gene cassette of [1](a) is 30% or more of the full length of the gene cassette;
[7] the expression vector of any one of [1] to [6], wherein the drug resistance gene of [1](a) is a neomycin phosphotransferase gene (NTP gene);
[8] a method for producing a transformant that has ability to produce a high level of a foreign gene-derived protein and to resist neomycin; which comprises the steps of inserting a foreign gene into the expression vector of [7], and transforming a host cell using the expression vector;
[9] a method for producing a foreign gene-derived protein, which comprises the steps of:
(a) inserting a foreign gene into the expression vector of [7];
(b) transforming a host cell with the expression vector;
(c) culturing the transformant in a medium supplemented with neomycin; and
(d) collecting the foreign gene-derived protein from the cultured transformant;
[10] the production method of [9], wherein a chemically defined medium (CD medium) or a medium supplemented with a non-animal-based additive to the CD medium is used for culturing in step (c) of [9];
[11] a method of screening for a transformant that has ability to produce a high level of a foreign gene-derived protein, which comprises the steps of:
(a) inserting a foreign gene into the expression vector of [7];
(b) transforming a host cell with the expression vector; and
(c) culturing the transformant in a medium supplemented with neomycin;

[12] the expression vector of any one of [1] to [6], wherein the drug resistance gene of [1](a) is a Zeocin resistance gene (Zeocin$^r$ gene);
[13] a method for producing a transformant that has ability to produce a high level of a foreign gene-derived protein and to resist Zeocin; which comprises the steps of inserting a foreign gene into the expression vector of [12], and transforming a host cell using the expression vector;
[14] a method for producing a foreign gene-derived protein, which comprises the steps of:
(a) inserting a foreign gene into the expression vector of [12];
(b) transforming a host cell with the expression vector;
(c) culturing the transformant in a medium supplemented with Zeocin; and
(d) collecting the foreign gene-derived protein from the cultured transformant;
[15] The production method of [14], wherein a chemically defined medium (CD medium) or a medium supplemented with a non-animal-based additive to the CD medium is used for culturing in step (c) of [14];
[16] a method of screening for a transformant that has ability to produce a high level of a foreign gene-derived protein, which comprises the steps of:
(a) inserting a foreign gene into the expression vector of [12];
(b) transforming a host cell with the expression vector; and
(c) culturing the transformant in a medium supplemented with Zeocin;
[17] the expression vector of any one of [1] to [6], wherein the drug resistance gene of [1](a) is a blasticidin resistance gene (Blasticidin gene);
[18] a method for producing a transformant that has ability to produce a high level of a foreign gene-derived protein and to resist blasticidin; which comprises the steps of inserting a foreign gene into the expression vector of [17], and transforming a host cell using the expression vector;
[19] a method for producing a foreign gene-derived protein, which comprises the steps of:
(a) inserting a foreign gene into the expression vector of [17];
(b) transforming a host cell with the expression vector;
(c) culturing the transformant in a medium supplemented with blasticidin; and
(d) collecting the foreign gene-derived protein from the cultured transformant;
[20] the production method of [19], wherein a chemically defined medium (CD medium) or a medium supplemented with a non-animal-based additive to the CD medium is used for culturing in step (c) of [19]; and
[21] a method of screening for a transformant that has ability to produce a high level of a foreign gene-derived protein, which comprises the steps of:
(a) inserting a foreign gene into the expression vector of [17];
(b) transforming a host cell with the expression vector; and
(c) culturing the transformant in a medium supplemented with blasticidin.

MODE FOR CARRYING OUT THE INVENTION

Figure 1:
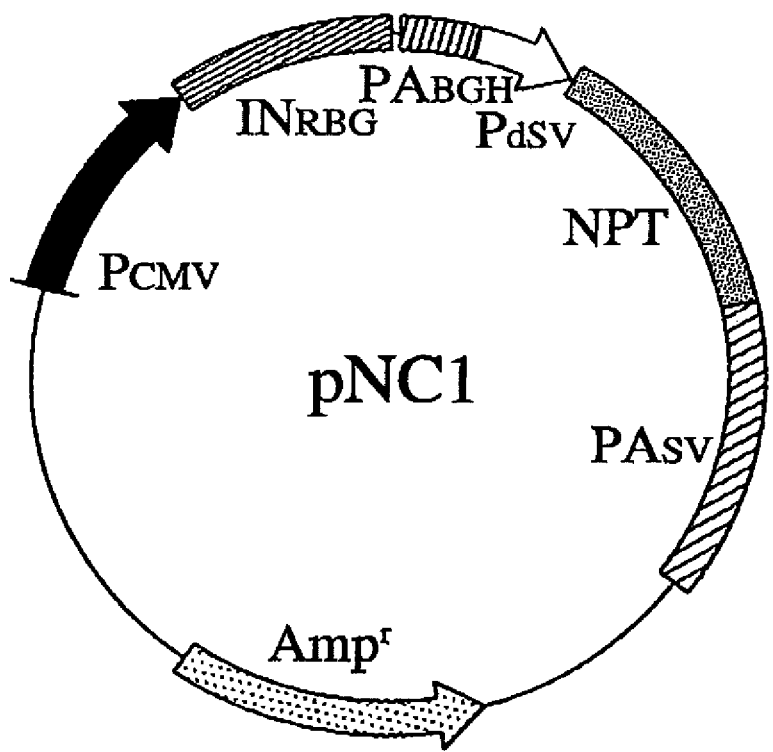
FIG. 1 shows the pNC1 construct. Each of the following indicates: PCMV: cytomegalovirus promoter; INRBG: rabbit growth hormone intron; PABGH: bovine growth hormone gene polyA additional signal; PdSV: enhancer-deleted simian virus 40 promoter; NPT: neomycin phosphotransferase cDNA; PASV: simian virus 40 polyA additional signal; and Amp$^r$: selection marker (ampicillin resistance) in *E. coli*.

By altering the codons of a drug resistance gene (NPT gene, Zeocin resistance gene, or blasticidin resistance gene) to the least frequently used codons in mammals to utterly attenuate the expression of the drug resistance gene, the present inventors made the survival under drug selection in medium (neomycin selection (for example G418), Zeocin selection, or blasticidin selection) difficult even for transformants unless the incorporated plasmid gene is integrated into a chromosome position with very high expression properties.

More specifically, the present invention provides expression vectors for inducing high-level production of recombinant proteins in mammalian host cells.

An expression vector of the present invention is constructed by including the following on a backbone vector:
(a) a translation-impaired drug resistance gene cassette, whose expression is weakened by altering codons to the least frequently used codons in a mammal; and
(b) a gene cassette comprising a cloning site for integration of a foreign gene between a highly transcriptionally-active promoter and a highly stable polyadenylation signal.

The present invention markedly impairs the expression mechanism of the drug resistance gene in the transformed host cell by altering the codons of a drug resistance gene to the least frequently used codons in mammals, and using promoters with decreased expression-inducing property of the drug resistance gene for the drug resistance gene cassette (cistron) construct. In the present invention, "gene cassette" refers to a unit with the basic composition of promoter, structural gene, and polyadenylation signal (polyAs) that expresses protein through transcription/translation, and it may also include as insertion sequences DNA sequences associated with any of these sequences or any optional DNA sequences. The drug resistance gene cassettes of the present invention are defined as "translation-impaired drug resistance gene cassette" because they differ from those with a simply attenuated promoter, and specifically allow acquirement of drug resistant strains having the plasmid gene integrated into the transcriptional hot spot. In the present invention, the drug resistance genes are not particularly limited, but preferred examples include a neomycin resistance gene (neomycin phosphotransferase gene, NTP gene), Zeocin resistance gene, or a blasticidin resistance gene.

In the present invention, "the least frequently used codons in mammals" refers to preferably, for example, the least frequently used codons in humans The least frequently used codons in humans include the codons disclosed in the document by Kim et al. (Gene, 199, p. 293, 1997). Specific examples of the codons are GCA for alanine, CGA for arginine, AAU for asparagine, GAU for aspartic acid, UGU for cysteine, CAA for glutamine, GAA for glutamic acid, GGU for glycine, CAU for histidine, UUA for leucine, AAA for lysine, CCA for proline, UUU for phenylalanine, UCA for serine, ACU for threonine, UAU for tyrosine, and/or GUA for valine, but are not limited thereto.

In the present invention, "to attenuate expression" indicates reducing gene expression at the transcription and/or translation levels, and specifically, this can be achieved by altering the codons to the above-mentioned "least frequently used codons in mammals".

In the above-mentioned "translation-impaired drug resistance gene cassette", the regions in which codons are altered are not particularly limited, but preferably, codons in a region corresponding to 30% or more (for example, 40% or more, 50% or more, 60% or more, 70% or more, 80% or more, 90% or more, 95% or more, or 100%) of the full length of the gene cassette are altered. The range of the codon-altered regions can be determined arbitrarily by considering other conditions of the vector.

As the promoter for the above-mentioned "translation-impaired drug resistance gene cassette", promoters derived from the promoter of a gene of a protein which is normally difficult to express in a mammalian cell, or promoters produced by deleting the enhancer from a normal promoter may be used. More specifically, a promoter produced by deleting the enhancer region from the SV40 virus antigen promoter (Mol. Cell. Biol., 6, p. 2593, 1986), or promoters with an equivalently very low expression property are preferably used.

Integration of plasmid DNA into a transcriptional hot spot on the host cell chromosome can be accomplished as a result by selection with neomycin (G418), Zeocin, blasticidin, or such according to the properties of the drug resistance gene cassette, but expression of the foreign gene-derived protein itself at the transcriptional hot spot of the chromosome must be strongly induced. Therefore, the promoters and polyadenylation signal (hereinafter, called polyA) in the multicloning site (hereinafter, referred to as MCS) where the protein genes are inserted will be selected from among those having the strongest expression-inducing property. Examples of the promoters include human cytomegalovirus immediate early (hCMV MIE: Cell, 41, p. 521, 1985) promoter, CMV5 promoter which is a fusion promoter of human cytomegalovirus promoter and adenovirus promoter (Nucleic Acid Research, 30, p. 2, 2002), and β-actin promoter (Proc. Natl. Acad. Sci. USA, 84, p. 4831, 1987); and examples of polyA include the bovine growth hormone-derived polyA sequence (DNA 5, p. 115, 1986). Herein, a DNA fragment carrying a multicloning site for inserting the gene of a protein of interest is called a "gene expression cassette".

Expression vectors of the present invention can be exemplified by expression vectors specifically described in the Examples, but are not limited thereto.

Furthermore, the present invention provides a method for producing transformants with an ability to produce foreign gene-derived proteins at high levels and an ability to resist drug, which comprises the steps of inserting a foreign gene into the above-mentioned expression vectors and transforming host cells using the expression vectors.

Specific examples include a method of obtaining transformants with high protein-producing ability, which involves inserting a foreign gene encoding a protein to be expressed into the multicloning site (hereinafter, referred to as MCS) of an expression vector of the present invention, then transforming host cells with the expression vector by using a transfection method (examples of the transfection method referred to herein include methods well known to those skilled in the art such as lipofectin method, electroporation method, calcium phosphate method, and microinjection method), and then selecting by drug (neomycin, Zeocin, or blasticidin) resistance.

In the present invention, the host cells are not particularly limited as long as they are cells suitable for expressing foreign gene-derived proteins, but preferably include, for example, mammalian cells, and more preferably Chinese hamster ovary cells (CHO cells).

Many of the transformed cells that survived drug selection have already achieved a relatively high protein expression level, but to select from these cells transformed cells that have an even higher level of production ability, the level of protein expression may be determined.

Furthermore, the present invention provides methods for producing a foreign gene-derived protein, which comprise the steps of:
(a) inserting a foreign gene into an expression vector of the present invention;
(b) transforming a host cell with the expression vector;
(c) culturing the transformant in a medium supplemented with a drug (neomycin, Zeocin, or blasticidin); and
(d) collecting the foreign gene-derived protein from the cultured transformant.

In the present invention, in step (c) mentioned above, transformants (colonies) showing high-efficiency protein expression can be selected by culturing in a medium supplemented with a drug (neomycin, Zeocin, or blasticidin). The selected transformants may be continuously cultured in the same medium, or they may be cultured after transferring to another medium such as a medium for large-scale expression.

In the present invention, media for culturing or naturalizing transformants are not particularly limited, but are for example, preferably a serum-free medium, and more preferably a CD medium or a CD medium supplemented with non-animal-based additives.

In the present invention, when collecting foreign gene-derived proteins from cultured transformants, the proteins may be purified by methods known to those skilled in the art (filtration, centrifugation, column purification, and such). The foreign gene-derived proteins can be expressed as fusion proteins with other proteins to facilitate purification.

Furthermore, the present invention provides a method of screening for transformants with high ability to produce a foreign gene-derived protein, which comprises the steps of:
(a) inserting a foreign gene into an expression vector of the present invention;
(b) transforming a host cell with the expression vector; and
(c) culturing the transformant in a medium supplemented with a drug (neomycin, Zeocin, or blasticidin).

All prior art documents cited in the specification are incorporated herein by reference.

EXAMPLES

Herein below, the present invention will be specifically described with reference to the Examples, but it is not to be constructed as being limited thereto.

Example 1

Construction of pNC1, pNC2, pNC5, pNC6, and pNC7

Figure 2:
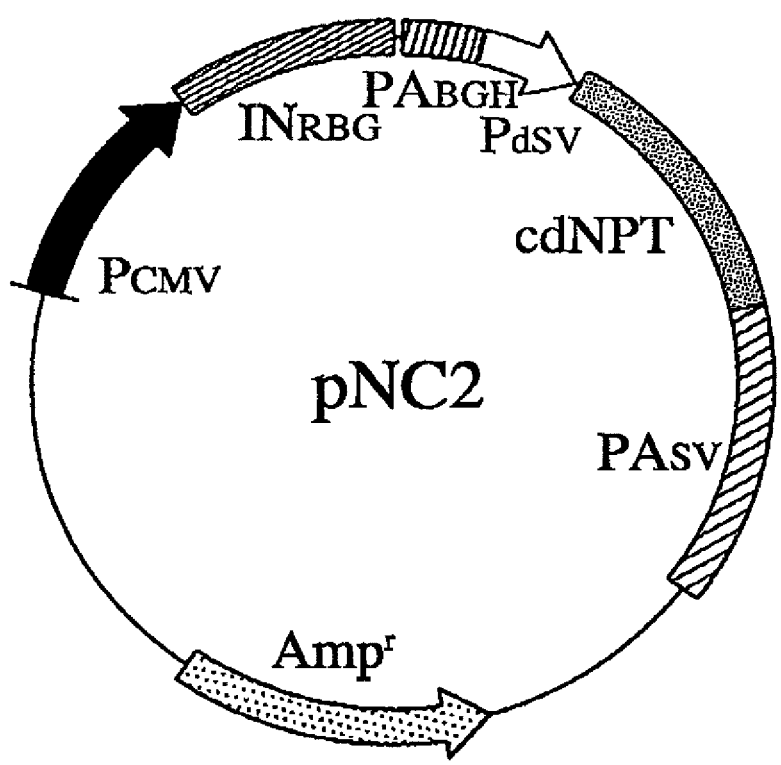
FIG. 2 shows the pNC2 construct. Each of the following indicates: PCMV: cytomegalovirus promoter; INRBG: rabbit growth hormone intron; PABGH: bovine growth hormone gene polyA additional signal; PdSV: enhancer-deleted simian virus 40 promoter; cdNPT: translation-impaired NPT gene produced by altering the codons of the entire NPT nucleotide sequence to the least frequently used codons in mammals; PASV: simian virus 40 polyA additional signal; and Amp$^r$: selection marker (ampicillin resistance) in E. coli.
Figure 3:
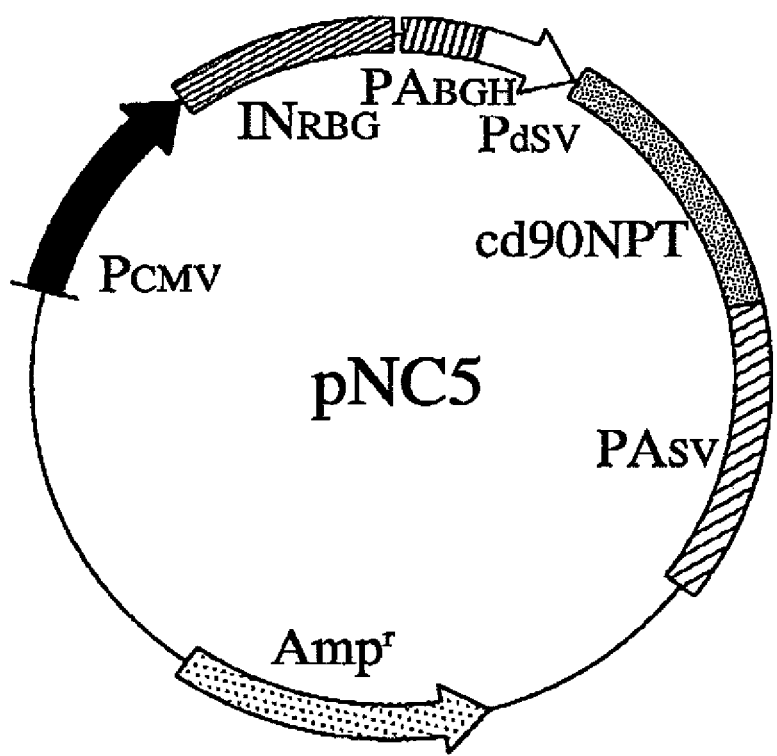
FIG. 3 shows the pNC5 construct. Each of the following indicates: PCMV: cytomegalovirus promoter; INRBG: rabbit growth hormone intron; PABGH: bovine growth hormone gene polyA additional signal; PdSV: enhancer-deleted simian virus 40 promoter; cd90NPT: translation-impaired NPT gene produced by altering codons in the range of 90 bases from the 5' end of the to the least frequently used codons in mammals; PASV: simian virus 40 polyA additional signal; and Amp$^r$: selection marker (ampicillin resistance) in E. coli.
Figure 4:
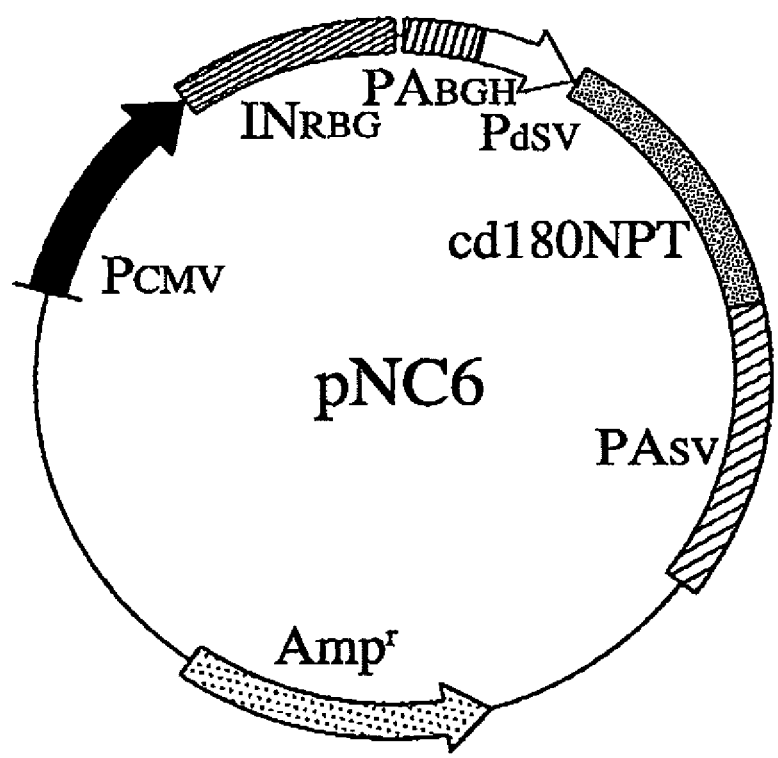
FIG. 4 shows the pNC6 construct. Each of the following indicates: PCMV: cytomegalovirus promoter; INRBG: rabbit growth hormone intron; PABGH: bovine growth hormone gene polyA additional signal; PdSV: enhancer-deleted simian virus 40 promoter; cd180NPT: translation-impaired NPT gene produced by altering codons in the range of 180 bases from the 5' end of the nucleotide sequence of NPT to the least frequently used codons in mammals; PASV: simian virus 40 polyA additional signal; and Amp$^r$: selection marker (ampicillin resistance) in E. coli.
Figure 5:
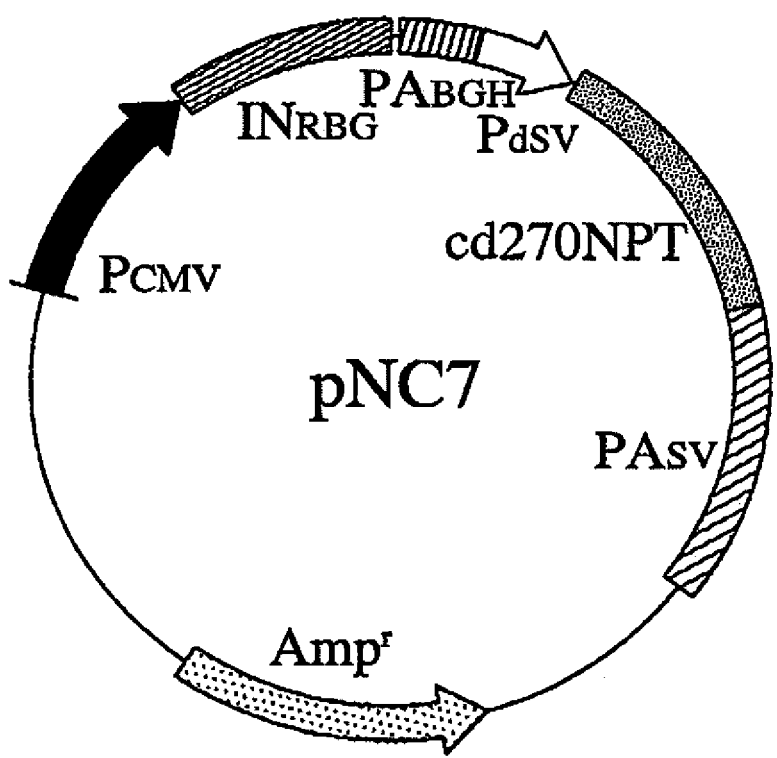
FIG. 5 shows the pNC7 construct. Each of the following indicates: PCMV: cytomegalovirus promoter; INRBG: rabbit growth hormone intron; PABGH: bovine growth hormone gene polyA additional signal; PdSV: enhancer-deleted simian virus 40 promoter; cd270NPT: translation-impaired NPT gene produced by altering codons in the range of 270 bases from the 5' end of the nucleotide sequence of NPT to the least frequently used codons in mammals; PASV: simian virus 40 polyA additional signal; and Amp$^r$: selection marker (ampicillin resistance) in E. coli.

Using methods well known to those skilled in the art, vectors of the present invention, pNC1, pNC2, pNC5, pNC6, and pNC7, were constructed. The entire nucleotide sequence of the backbone vector pNC1 is shown in SEQ ID NO: 1. pNC1 carries the wild-type NPT cDNA between nucleotides No. 1784 and No. 2578 (FIG. 1).

pNC2 is constructed by substituting nucleotides No. 1784 to No. 2578 in the sequence of pNC1 with the sequence of SEQ ID NO: 2. The substituted region of pNC2 is introduced with a translation-impaired NPT gene in which the codons of the entire nucleotide sequence of NPT have been altered to the least frequently used codons in mammals (FIG. 2).

pNC5 is constructed by substituting nucleotides No. 1784 to No. 2578 in the sequence of pNC1 with the sequence of SEQ ID NO: 3. The substituted region of pNC5 is introduced with a translation-impaired NPT gene in which codons in the range of 90 bases from the 5' end (11.3% codon alteration) of the NPT nucleotide sequence have been altered to the least frequently used codons in mammals (FIG. 3).

pNC6 is constructed by substituting nucleotides No. 1784 to No. 2578 in the sequence of pNC1 with the sequence of SEQ ID NO: 4. The substituted region of pNC6 is introduced with a translation-impaired NPT gene in which codons in the range of 180 bases from the 5' end (22.6% codon alteration) of the NPT nucleotide sequence have been altered to the least frequently used codons in mammals (FIG. 4).

pNC7 is constructed by substituting nucleotides No. 1784 to No. 2578 in the sequence of pNC1 with the sequence of SEQ ID NO: 5. The substituted region of pNC7 is introduced with a translation-impaired NPT gene in which codons in the range of 270 bases from the 5' end (34.0% codon alteration) of the NPT nucleotide sequence have been altered to the least frequently used codons in mammals (FIG. 5).

Example 2

Construction of pNC1/hMBL, pNC2/hMBL, pNC5/hMBL, pNC6/hMBL, and pNC7/hMBL

Figure 6:
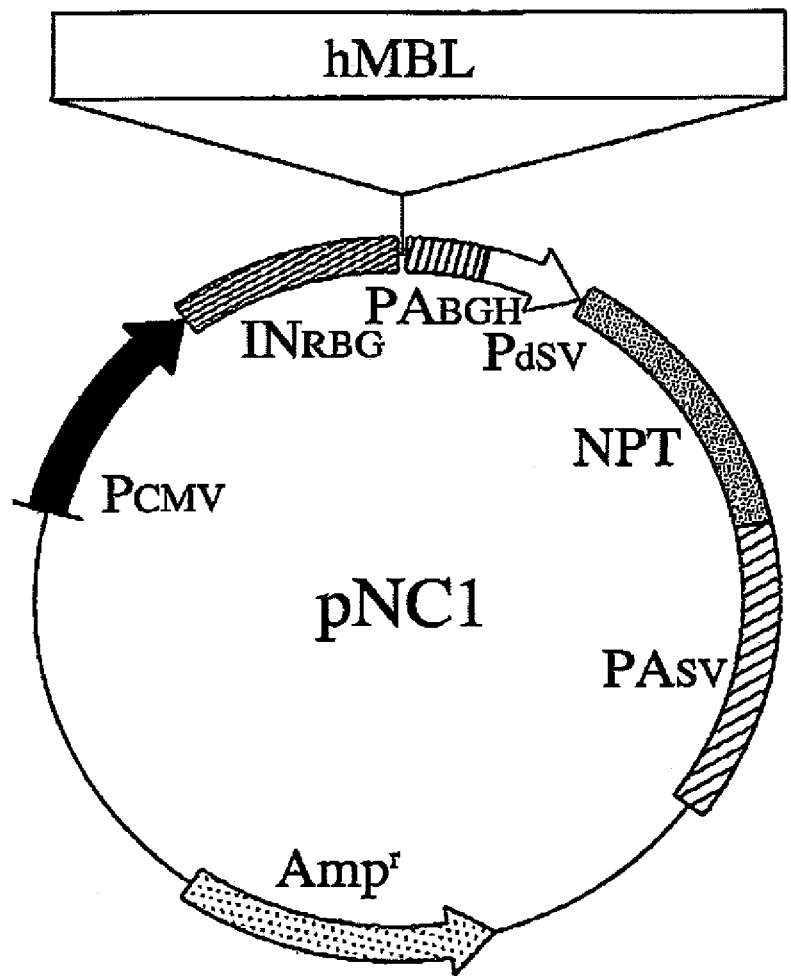
FIG. 6 shows the pNC1/hMBL construct. Each of the following indicates: PCMV: cytomegalovirus promoter; INRBG: rabbit growth hormone intron; hMBL: human mannose-binding lectin cDNA; PABGH: bovine growth hormone gene polyA additional signal; PdSV: enhancer-deleted simian virus 40 promoter; NPT: neomycin phosphotransferase cDNA; PASV: simian virus 40 polyA additional signal; and Amp$^r$: selection marker (ampicillin resistance) in E. coli.
Figure 7:
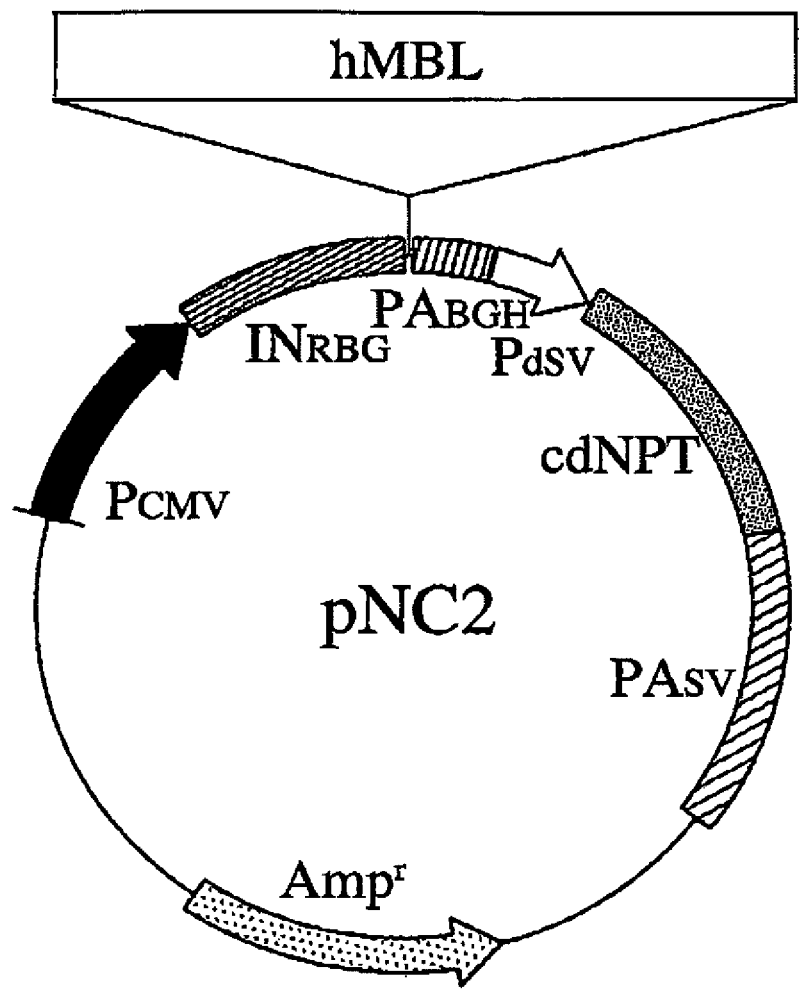
FIG. 7 shows the pNC2/hMBL construct. Each of the following indicates: PCMV: cytomegalovirus promoter; INRBG: rabbit growth hormone intron; hMBL: human mannose-binding lectin cDNA; PABGH: bovine growth hormone gene polyA additional signal; PdSV: enhancer-deleted simian virus 40 promoter; cdNPT: translation-impaired NPT gene produced by altering the codons of the entire NPT nucleotide sequence to the least frequently used codons in mammals; PASV: simian virus 40 polyA additional signal; and Amp$^r$: selection marker (ampicillin resistance) in E. coli.
Figure 8:
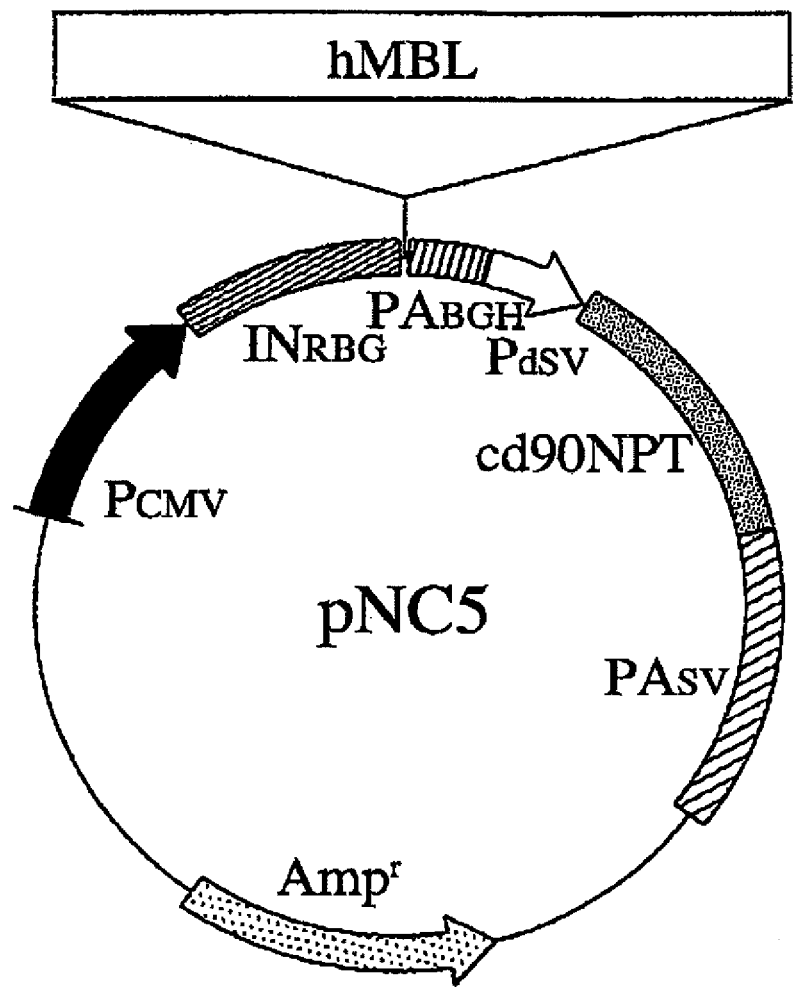
FIG. 8 shows the pNC5/hMBL construct. Each of the following indicates: PCMV: cytomegalovirus promoter; INRBG: rabbit growth hormone intron; hMBL: human mannose-binding lectin cDNA; PABGH: bovine growth hormone gene polyA additional signal; PdSV: enhancer-deleted simian virus 40 promoter; cd90NPT: translation-impaired NPT gene produced by altering codons in the range of 90 bases from the 5' end of the nucleotide sequence of NPT to the least frequently used codons in mammals; PASV: simian virus 40 polyA additional signal; and Amp$^r$: selection marker (ampicillin resistance) in E. coli.
Figure 9:
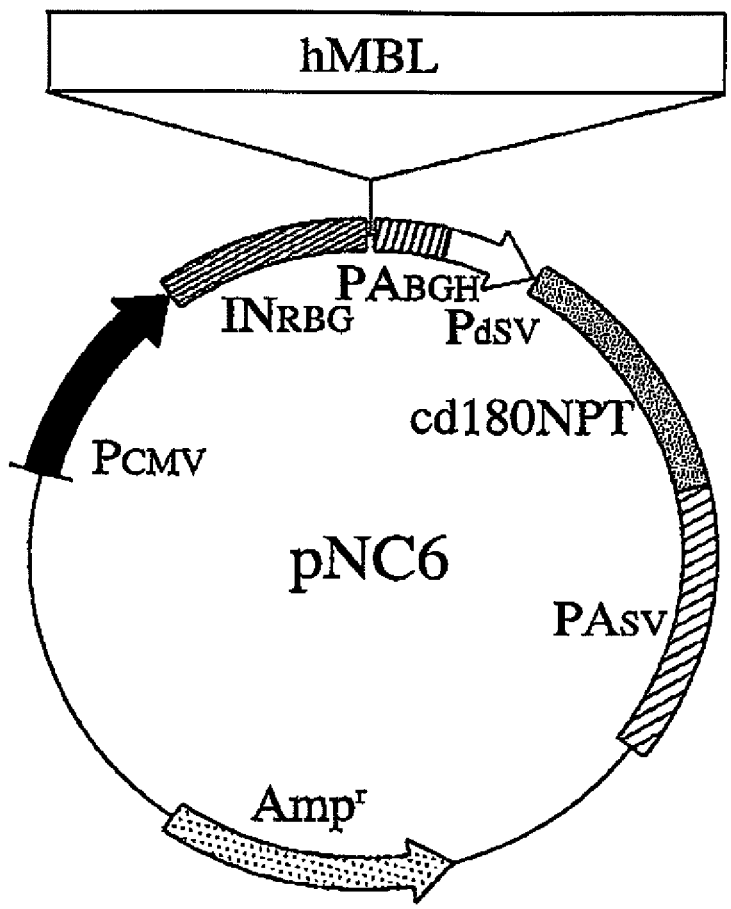
FIG. 9 shows the pNC6/hMBL construct. Each of the following indicates: PCMV: cytomegalovirus promoter; INRBG: rabbit growth hormone intron; hMBL: human mannose-binding lectin cDNA; PABGH: bovine growth hormone gene polyA additional signal; PdSV: enhancer-deleted simian virus 40 promoter; cd180NPT: translation-impaired NPT gene produced by altering codons in the range of 180 bases from the 5' end of the nucleotide sequence of NPT to the least frequently used codons in mammals; PASV: simian virus 40 polyA additional signal; and Amp$^r$: selection marker (ampicillin resistance) in E. coli.
Figure 10:
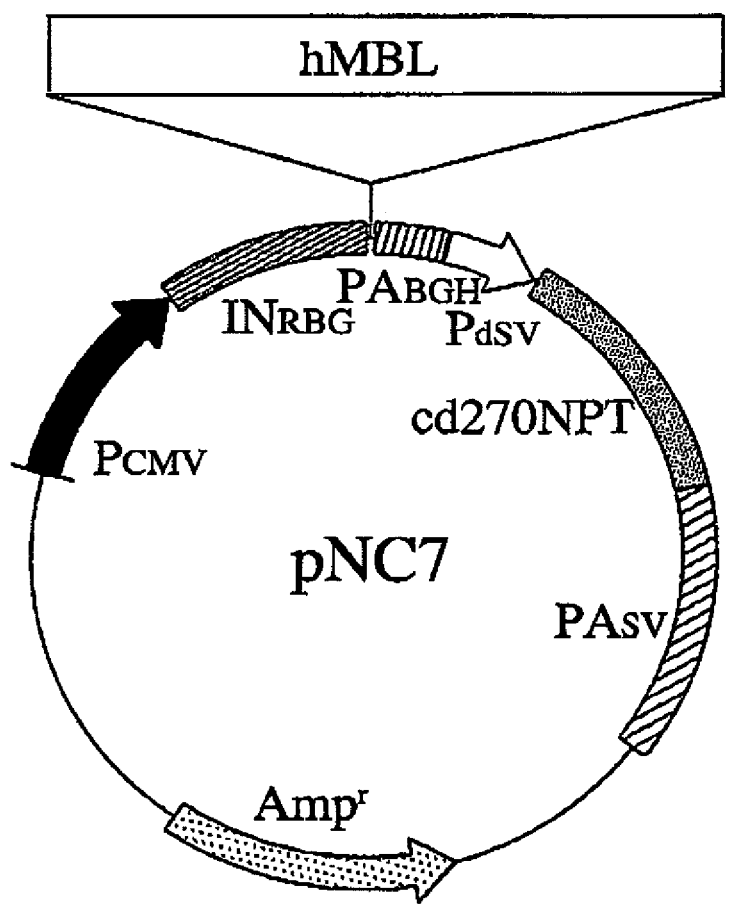
FIG. 10 shows the pNC7/hMBL construct. Each of the following indicates: PCMV: cytomegalovirus promoter; INRBG: rabbit growth hormone intron; hMBL: human mannose-binding lectin cDNA; PABGH: bovine growth hormone gene polyA additional signal; PdSV: enhancer-deleted simian virus 40 promoter; cd270NPT: translation-impaired NPT gene produced by altering codons in the range of 270 bases from the 5' end of the nucleotide sequence of NPT to the least frequently used codons in mammals; PASV: simian virus 40 polyA additional signal; and Amp$^r$: selection marker (ampicillin resistance) in E. coli.

Using methods well known to those skilled in the art, nucleotides No. 1267 to No. 1275 in the vectors of the present invention, pNC1, pNC2, pNC5, pNC6, and pNC7, were substituted with a cDNA encoding the human mannan-binding lectin (MBL) of SEQ ID NO: 6 (hereinafter referred to as hMBL), to construct pNC1/hMBL (FIG. 6), pNC2/hMBL (FIG. 7), pNC5/hMBL (FIG. 8), pNC6/hMBL (FIG. 9), and pNC7/hMBL (FIG. 10).

Example 3

Transfection of pNC1/hMBL, pNC2/hMBL, pNC5/hMBL, pNC6/hMBL, and pNC7/hMBL into CHO Cells, and G418 Selection Using a CD Medium or a CD Medium Supplemented with Non-Animal-Based Additives 10 μg of pNC1/hMBL, pNC2/hMBL, pNC5/hMBL, pNC6/hMBL, and pNC7/hMBL were transfected into $5.0 \times 10^5$ CHO cells (CHO DG44 cells) in 25 cm²-culture flasks using the Lipofectin method (using Lipofectamine™ LTX; Invitrogen). Gene transfection was performed according to the manufacturer's instructions. 48 hours after gene transfection, the number of cells were counted, and then the cells were diluted in an IS CHO-CD w/Hydrolysate medium (IS Japan) supplemented with 4 mM Gluta MAX™-I (Invitrogen). The cells were plated into five 96-well microtiter plates each at concentrations of 1,000 cells/well and 100 cells/well, a total of 10 plates (960 wells), and after culturing in the presence of 5% carbon dioxide gas at 37° C. for approximately three weeks, viable cells were observed (G418-resistant clone). G418-resistant clones were arbitrarily selected from the viable cells, transferred to 24-well plates together with the IS CHO-CD w/Hydrolysate medium (IS Japan) supplemented with 4 mM Gluta MAX™-I (Invitrogen), and cultured until the cells occupied ⅓ or more of each well. 0.4 mL of each clone was placed into a sterile tube and centrifuged at 200×g for two minutes. The supernatant was discarded, and the cells were suspended in 0.1 mL of fresh medium (IS CHO-CD w/Hydrolysate medium (IS Japan) supplemented with 4 mM Gluta MAX™-I (Invitrogen)). After counting the number of cells, the cells were diluted with the medium to $5.0 \times 10^5$ cells/mL, then 0.2 mL of them were transferred to new 24-well plates, the cells were cultured in the presence of 5% carbon dioxide gas at 37° C. for 72 hours. Then, the cells were centrifuged at 9,300×g for two minutes and supernatant was collected. Next, the production level of MBL in the culture supernatants was determined.

Example 4

Determination of the MBL Production Levels by pNC1/hMBL, pNC5/hMBL, pNC6/hMBL, and pNC7/hMBL Transfected Clones The production level was assayed by ELISA. 96-well plates (F96 MAXI SORP Nunc-Immunoplate, Cat. no. 442404, Nunc) were coated with 1 μg/mL of anti-human MBL antibody (gift from Dr. Ohtani at Asahikawa Medical University, Japan) diluted with a coating buffer (15 mM $Na_2CO_3$, 35 mM $NaHCO_3$, 0.05% $NaN_3$, pH 9.6) at 4° C. for 16 hours. After blocking with 4% Block Ace (Dainippon Sumitomo Pharma Co., Ltd.), the 72-hour culture supernatant (1/1,000 to 1/100,000 dilution), two-fold dilution series (0.3125 to 20 ng/mL) of purified human MBL (gift from Dr. Ohtani at Asahikawa Medical University, Japan) in IS CHO-CD w/Hydrolysate medium (IS Japan) which is a serum-free medium for CHO cells, or IS CHO with Hydrolysate medium (IS Japan) was applied to the plates at 100 μL/well, and the plates were incubated at 37° C. for one hour. This was further incubated with 0.1 μg/mL of biotinylated human MBL monoclonal antibody (gift from Dr. Ohtani at Asahikawa Medical University, Japan) at 37° C. for one hour. VECTASTAIN Elite ABC Kit STANDARD (2 drops of Reagent A, 2 drops of Regent B/5 mL, Vector), which had been incubated at 37° C. for 30 minutes, was applied at 100 μL/well, and this was allowed to react at 37° C. for 45 minutes. PEROXIDASE SUBSTRATE KIT TMB (2 drops of Buffer, 3 drops of TMB, 2 drops of HYDROGEN PEROXIDE/5 mL, Vector), which had been incubated at room temperature for 30 minutes, was further applied at 100 μL/well, and after letting this react at room temperature for 15 minutes, 1 M phosphoric acid was added at 100 μL/well to stop the reaction. Protein concentration was determined using a microplate reader (Model 680, manufactured by BioRad). Results obtained by the ELISA method, and the top three samples showing high human MBL production levels are shown in Table 1. The clone with the highest production level showed significantly high productivity compared to the vector with the unaltered codons.

TABLE 1

| hMBL production in G418-resistant clone | |
|---|---|
| Clone name | Amount of production (μg/ml) |
| pNC1-1 | 14.9 |
| pNC1-17 | 13.2 |
| pNC1-49 | 12.2 |
| pNC2-23 | 14.7 |
| pNC2-37 | 20.0 |
| pNC2-48 | 23.3 |
| pNC5-2 | 9.2 |
| pNC5-3 | 9.5 |
| pNC5-5 | 9.9 |

TABLE 1-continued hMBL production in G418-resistant clone

| Clone name | Amount of production (μg/ml) |
|---|---|
| pNC6-7 | 13.7 |
| pNC6-21 | 16.0 |
| pNC6-24 | 11.5 |
| pNC7-5 | 32.5 |
| pNC7-29 | 36.4 |
| pNC7-30 | 46.1 |

Example 5 hMBL Production Levels by pNC1/hMBL, pNC2/hMBL, pNC5/hMBL, pNC6/hMBL, and pNC7/hMBL Transfected Cell Clones The distribution of hMBL expressed by the pNC1, pNC2, pNC5, pNC6, and pNC7 expression vectors of the present invention in each clone is shown in Table 2.

For pNC1, among the fifty G418-resistant strains, 72.0% produced hMBL at 0 μg/mL or more to less than 5 μg/mL. Fourteen out of the fifty strains (28.0%) showed production levels of 5 μg/mL or more. Seven out of the fifty strains (14.0%) showed production levels of 10 μg/mL or more. The strain showing the highest production level yielded 15.0 μg/mL in 3 days.

For pNC2, among the fifty G418-resistant strains, 40.0% produced hMBL at 0 μg/mL or more to less than 5 μg/mL. Thirty out of the fifty strains (60.0%) showed production levels of 5 μg/mL or more. Fourteen out of the fifty strains (28.0%) showed production levels of 10 μg/mL or more. Two out of the fifty strains (4.0%) showed production levels of 15 μg/mL or more. The strain showing the highest production level yielded 23.3 μg/mL in 3 days.

For pNC5, among the fifty G418-resistant strains, 70.0% produced hMBL at 0 μg/mL or more to less than 5 μg/mL. Fifteen out of the fifty strains (30.0%) showed production levels of 5 μg/mL or more. The strain showing the highest production level yielded 9.9 μg/mL in 3 days.

For pNC6, among the fifty G418-resistant strains, 60.0% produced hMBL at 0 μg/mL or more to less than 5 μg/mL. Twenty out of the fifty strains (40.0%) showed production levels of 5 μg/mL or more. Four out of the fifty strains (8.0%) showed production levels of 10 μg/mL or more. One out of fifty strains (2.0%) showed production levels of 15 μg/mL or more. The strain showing the highest production level yielded 16.0 μg/mL in 3 days.

For pNC7, among the fifty G418-resistant strains, 56.0% produced hMBL at 0 μg/mL or more to less than 5 μg/mL. Twenty-two out of the fifty strains (44.0%) showed production levels of 5 μg/mL or more. Sixteen out of the fifty strains (32.0%) showed production levels of 10 μg/mL or more. Surprisingly, thirteen out of fifty strains (26.0%) showed production levels of 15 μg/mL or more. The strain showing the highest production level yielded 46.1 μg/mL in 3 days.

This was of the highest level when compared to the initial clone data before gene amplification by representative expression vectors reported in the literature (DNA, 7, p. 651, 1988; Biotechnology, 10, p. 1455, 1992; Biotechnology, 8, p. 662, 1990; Gene 76, p. 19, 1989; and Biotechnology, 9, p. 64, 1991).

Screening of recombinant cells by gene amplification usually requires six months to a year. Since there are large variations due to culturing conditions and amplification stimulating agent concentrations, it is considered appropriate to compare the primary efficiency of the expression vectors using the pre-amplification expression level of the initial clones. This revealed that the efficiency of the expression vectors of the present invention is very high. The results confirmed that while the vectors of the present invention yield very few G418-resistant strains, they enable establishment of cell strains that are capable of producing high levels of proteins of interest with very high efficiency. This proved that expression vectors of the present invention enable very high levels of protein expression.

TABLE 2

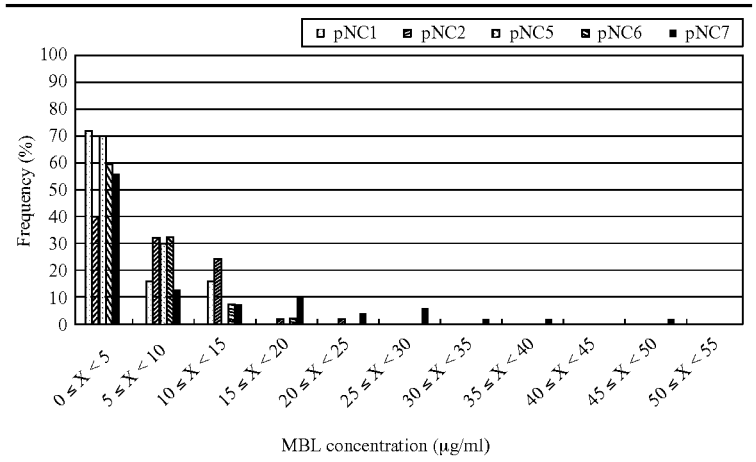

Example 6

Construction of pZC1, pZC2, pZC5, and pZC7

Figure 11:
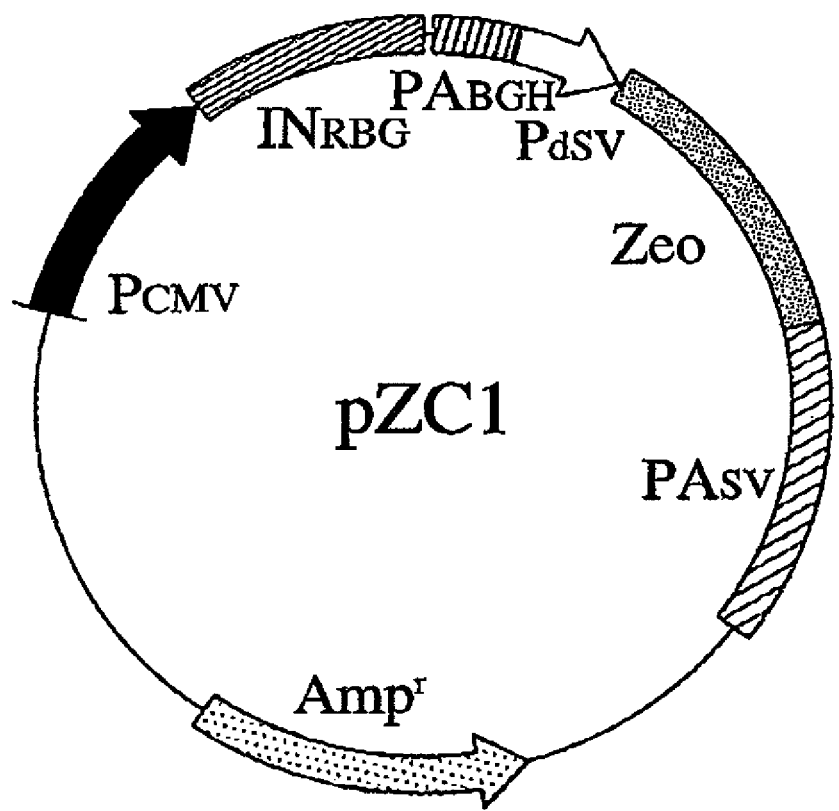
FIG. 11 shows the pZC1 construct. Each of the following indicates: PCMV: cytomegalovirus promoter; INRBG: rabbit growth hormone intron; PABGH: bovine growth hormone gene polyA additional signal; PdSV: enhancer-deleted simian virus 40 promoter; Zeo: Zeocin resistance gene (Sh ble gene) cDNA; PASV: simian virus 40 polyA additional signal; and Amp$^r$: selection marker (ampicillin resistance) in E. coli.
Figure 12:
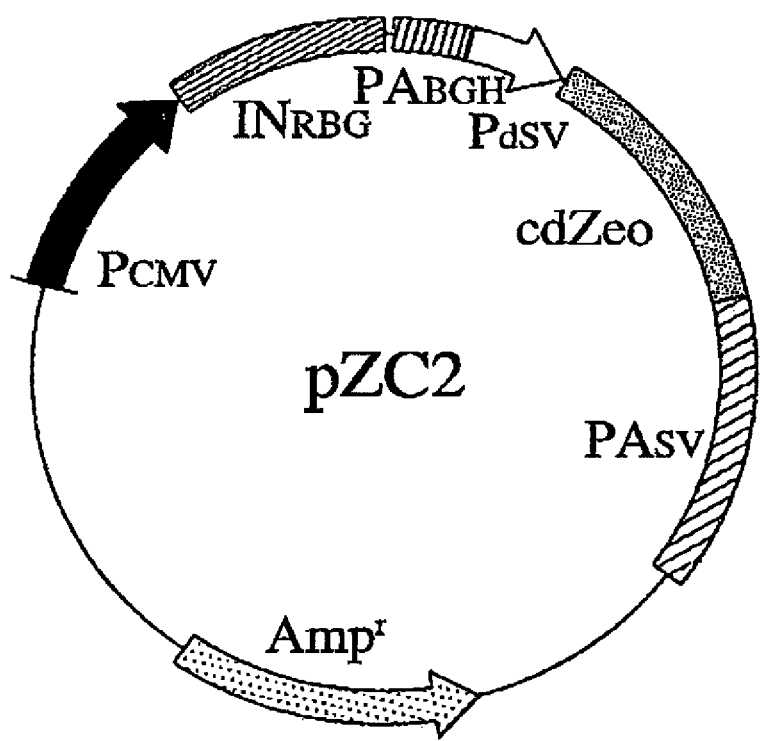
FIG. 12 shows the pZC2 construct. Each of the following indicates: PCMV: cytomegalovirus promoter; INRBG: rabbit growth hormone intron; PABGH: bovine growth hormone gene polyA additional signal; PdSV: enhancer-deleted simian virus 40 promoter; cdZeo: translation-impaired Zeocin resistance gene (Sh ble gene) produced by altering the codons of the entire Zeocin resistance gene nucleotide sequence to the least frequently used codons in mammals; PASV: simian virus 40 polyA additional signal; and Amp$^r$: selection marker (ampicillin resistance) in E. coli.
Figure 13:
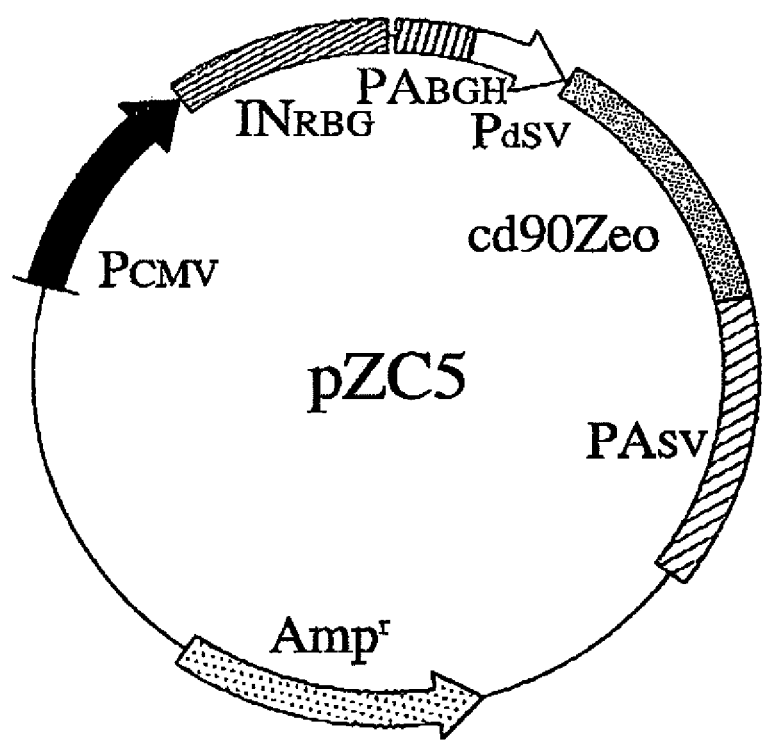
FIG. 13 shows the pZC5 construct. Each of the following indicates: PCMV: cytomegalovirus promoter; INRBG: rabbit growth hormone intron; PABGH: bovine growth hormone gene polyA additional signal; PdSV: enhancer-deleted simian virus 40 promoter; cd90Zeo: translation-impaired Zeocin resistance gene (Sh ble gene) produced by altering codons in the range of 90 bases from the 5' end of the nucleotide sequence of the Zeocin resistance gene to the least frequently used codons in mammals; PASV: simian virus 40 polyA additional signal; and Amp$^r$: selection marker (ampicillin resistance) in E. coli.
Figure 14:
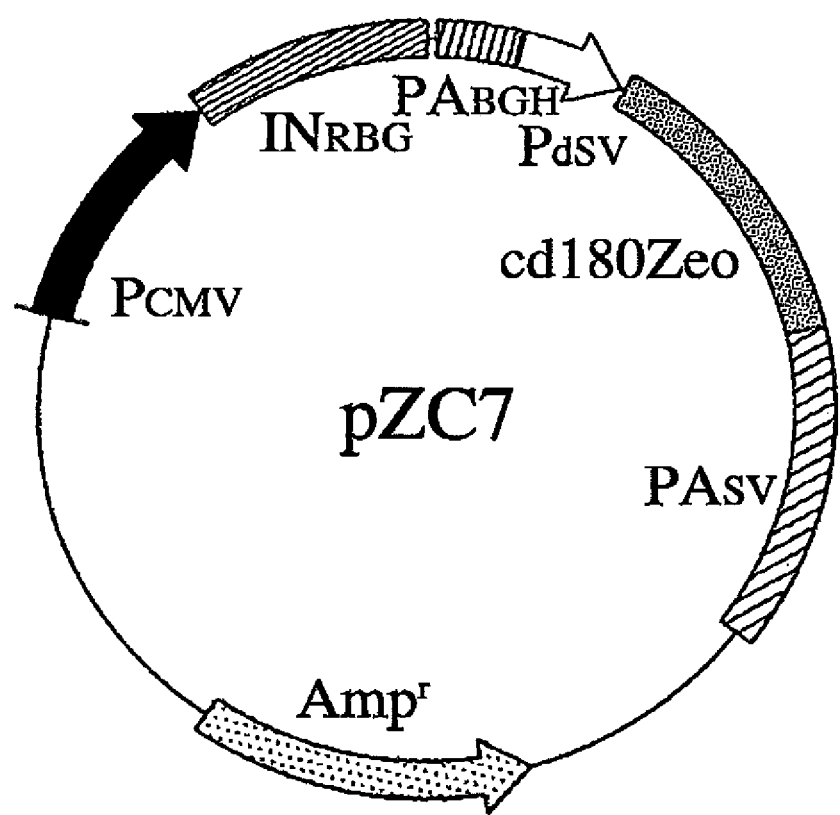
FIG. 14 shows the pZC7 construct. Each of the following indicates: PCMV: cytomegalovirus promoter; INRBG: rabbit growth hormone intron; PABGH: bovine growth hormone gene polyA additional signal; PdSV: enhancer-deleted simian virus 40 promoter; cd180Zeo: translation-impaired Zeocin resistance gene (Sh ble gene) produced by altering codons in the range of 180 bases from the 5' end of the nucleotide sequence of the Zeocin resistance gene to the least frequently used codons in mammals; PASV: simian virus 40 polyA additional signal; and Amp$^r$: selection marker (ampicillin resistance) in E. coli.

Using methods well known to those skilled in the art, pZC1, pZC2, pZC5, and pZC7, which are vectors of the present invention, were constructed. pZC1 carries the wild-type Zeocin resistance gene (Sh ble gene) described in SEQ ID NO: 7 between nucleotides No. 1784 to No. 2578 in the sequence of backbone vector pNC1 (FIG. 11). pZC2 is constructed by substituting nucleotides No. 1784 to No. 2578 in the nucleotide sequence of pNC1 with the sequence of SEQ ID NO: 8. The substituted region of pZC2 is introduced with a translation-impaired Zeocin resistance gene in which codons in the nucleotide sequence of the Zeocin resistance gene have been altered to the least frequently used codons in mammals (FIG. 12).

pZC5 is constructed by substituting nucleotides No. 1784 to No. 2578 in the sequence of pNC1 with the sequence of SEQ ID NO: 9. The substituted region of pZC5 is introduced with a translation-impaired Zeocin resistance gene in which codons in the range of 90 bases from the 5' end (24.0% codon alteration) of the nucleotide sequence of the Zeocin resistance gene have been altered to the least frequently used codons in mammals (FIG. 13).

pZC7 is constructed by substituting nucleotides No. 1784 to No. 2578 in the sequence of pNC1 with the sequence of SEQ ID NO: 10. The substituted region of pZC7 is introduced with a translation-impaired Zeocin resistance gene in which codons in the range of 180 bases from the 5' end (48.0% codon alteration) of the nucleotide sequence of the Zeocin resistance gene have been altered to the least frequently used codons in mammals (FIG. 14).

Example 7

Construction of pZC1/hMBL, pZC2/hMBL, pZC5/hMBL, and pZC7/hMBL

Figure 15:
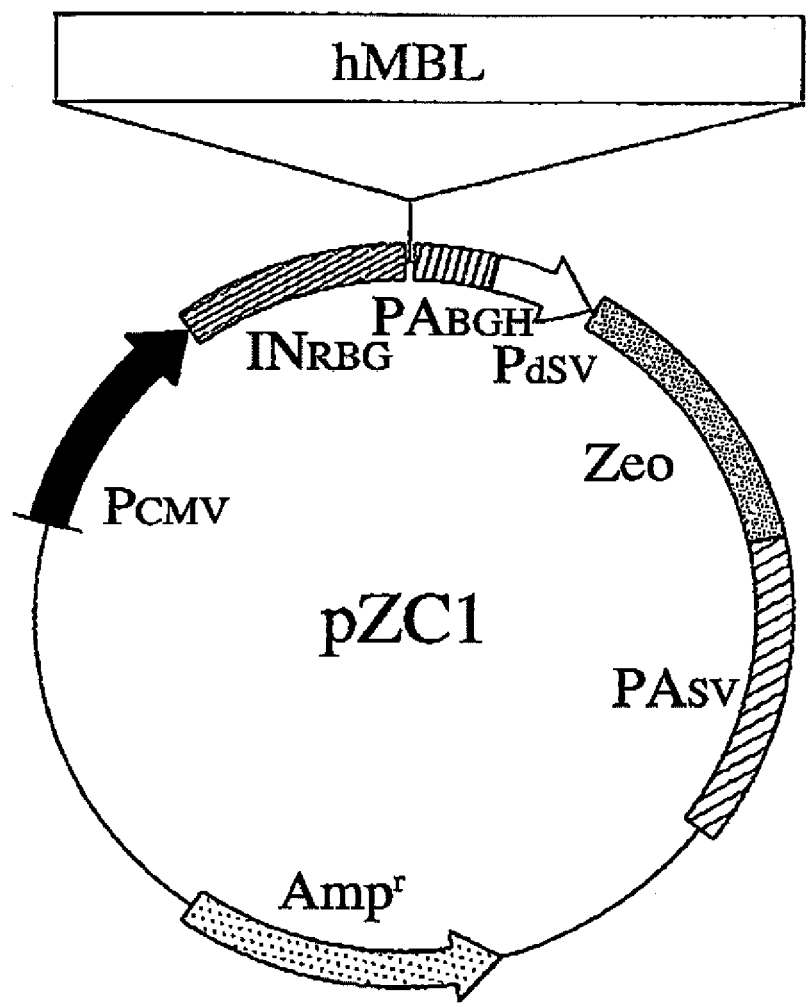
FIG. 15 shows the pZC1/hMBL construct. Each of the following indicates: PCMV: cytomegalovirus promoter; INRBG: rabbit growth hormone intron; hMBL: human mannose-binding lectin cDNA; PABGH: bovine growth hormone gene polyA additional signal; PdSV: enhancer-deleted simian virus 40 promoter; Zeo: Zeocin resistance gene (Sh ble gene) cDNA; PASV: simian virus 40 polyA additional signal; and Amp$^r$: selection marker (ampicillin resistance) in E. coli.
Figure 16:
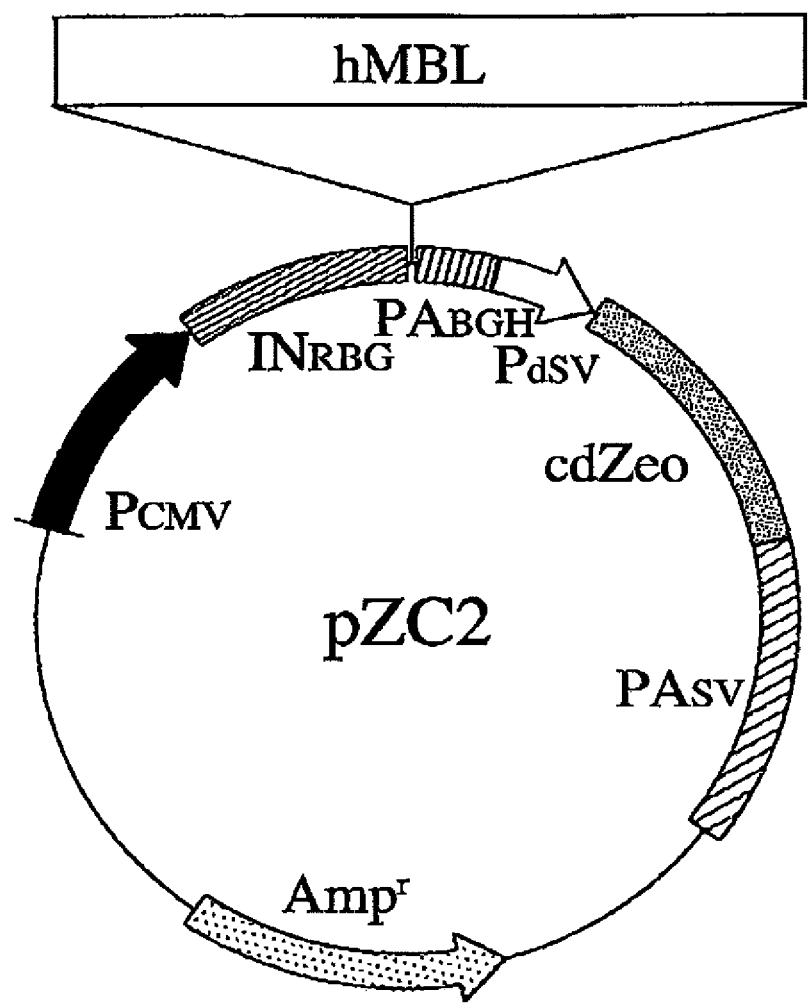
FIG. 16 shows the pZC2/hMBL construct. Each of the following indicates: PCMV: cytomegalovirus promoter; INRBG: rabbit growth hormone intron; hMBL: human mannose-binding lectin cDNA; PABGH: bovine growth hormone gene polyA additional signal; PdSV: enhancer-deleted simian virus 40 promoter; cdZeo: translation-impaired Zeocin resistance gene (Sh ble gene) produced by altering codons of the entire Zeocin resistance gene nucleotide sequence to the least frequently used codons in mammals; PASV: simian virus 40 polyA additional signal; and Amp[r]: selection marker (ampicillin resistance) in E. coli.
Figure 17:
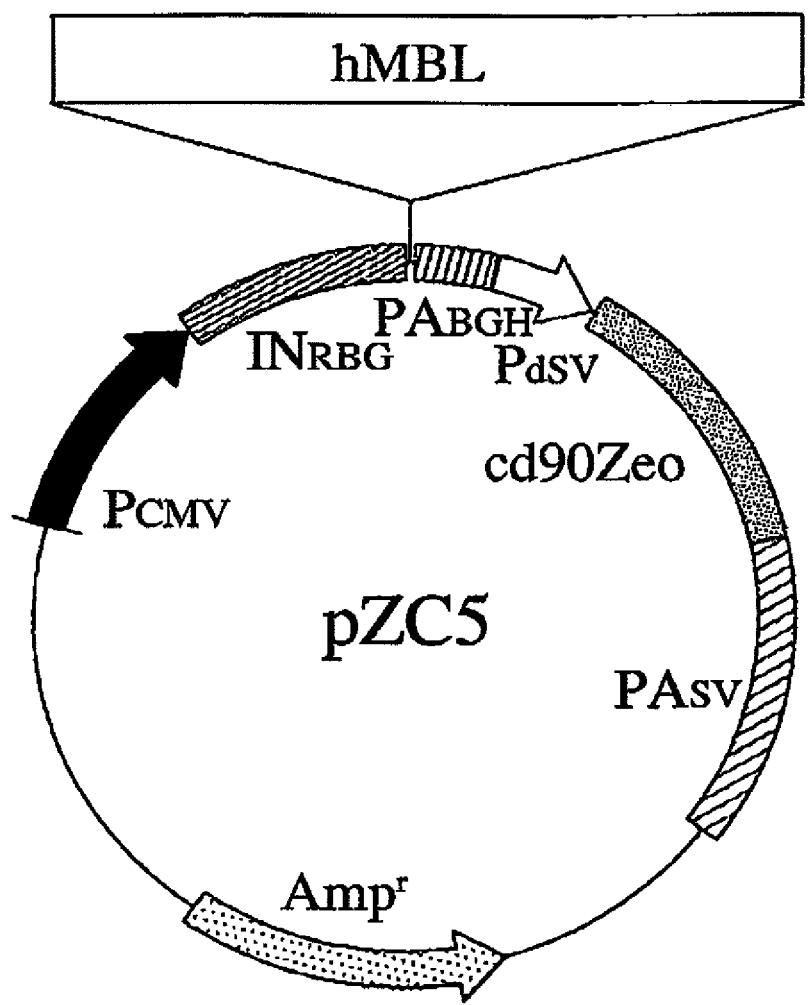
FIG. 17 shows the pZC5/hMBL construct. Each of the following indicates: PCMV: cytomegalovirus promoter; INRBG: rabbit growth hormone intron; hMBL: human mannose-binding lectin cDNA; PABGH: bovine growth hormone gene polyA additional signal; PdSV: enhancer-deleted simian virus 40 promoter; cd90Zeo: translation-impaired Zeocin resistance gene (Sh ble gene) produced by altering codons in the range of 90 bases from the 5' end of the nucleotide sequence of Zeocin resistance gene to the least frequently used codons in mammals; PASV: simian virus 40 polyA additional signal; and Amp[r]: selection marker (ampicillin resistance) in E. coli.
Figure 18:
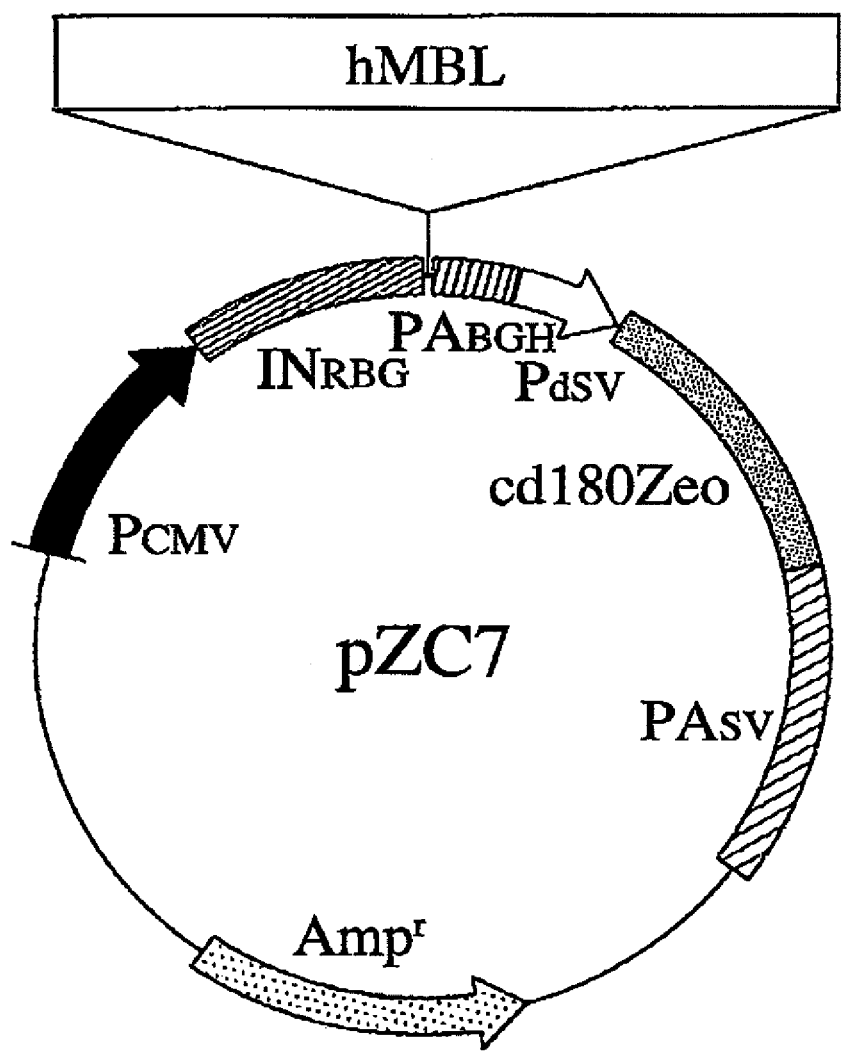
FIG. 18 shows the pZC7/hMBL construct. Each of the following indicates: PCMV: cytomegalovirus promoter; INRBG: rabbit growth hormone intron; hMBL: human mannose-binding lectin cDNA; PABGH: bovine growth hormone gene polyA additional signal; PdSV: enhancer-deleted simian virus 40 promoter; cd180Zeo: translation-impaired Zeocin resistance gene (Sh ble gene) produced by altering codons in the range of 180 bases from the 5' end of the nucleotide sequence of the Zeocin resistance gene to the least frequently used codons in mammals; PASV: simian virus 40 polyA additional signal; and Amp[r]: selection marker (ampicillin resistance) in E. coli.

Using methods well known to those skilled in the art, nucleotides No. 1267 to No. 1275 of vectors of the present invention, pZC1, pZC2, pZC5, and pZC7, were substituted with a cDNA encoding the human mannan-binding lectin (MBL) of SEQ ID NO: 6 (hereinafter referred to as hMBL), to construct pZC1/hMBL (FIG. 15), pZC2/hMBL (FIG. 16), pZC5/hMBL (FIG. 17), and pZC7/hMBL (FIG. 18).

Example 8

Transfection of pZC1/hMBL, pZC2/hMBL, pZC5/hMBL, and pZC7/hMBL into CHO Cells, and Zeocin Selection Using a CD Medium or a CD Medium Supplemented with Non-Animal-Based Additives 10 µg of pZC1/hMBL, pZC2/hMBL, pZC5/hMBL, and pZC7/hMBL were transfected into $5.0 \times 10^5$ CHO cells (CHO DG44 cells) in 25 cm$^2$-culture flasks using the Lipofectin method (using Lipofectamine™ LTX; Invitrogen). Gene transfection was performed according to the manufacturer's instructions. 48 hours after gene transfection, the number of cells were counted, and then the cells were diluted in an IS CHO-CD w/Hydrolysate medium (IS Japan) supplemented with 4 mM Gluta MAX™-I (Invitrogen) and 200 µg/mL Zeocin (Invitrogen). The cells were plated into five 96-well microtiter plates (480 wells) at a concentration of 4,000 cells/well, and after culturing in the presence of 5% carbon dioxide gas at 37° C. for approximately three weeks, surviving cells were observed (Zeocin-resistant clone). Zeocin-resistant clones were arbitrarily selected from the surviving cells, transferred to 24-well plates together with the IS CHO-CD w/Hydrolysate medium (IS Japan) supplemented with 4 mM Gluta MAX™-I (Invitrogen) and 200 µg/mL Zeocin (Invitrogen), and cultured until the cells occupied ⅓ or more of each well. 0.4 mL of each clone was taken into a sterile tube and centrifuged at 200×g for two minutes. The supernatant was discarded, and the cells were suspended in 0.1 mL of fresh medium (IS CHO-CD w/Hydrolysate medium (IS Japan) supplemented with 4 mM Gluta MAX™-I (Invitrogen)). After counting the number of cells, the cells were diluted with the medium to $5.0 \times 10^5$ cells/mL, then 0.2 mL of them were transferred to new 24-well plates, the cells were cultured in the presence of 5% carbon dioxide gas at 37° C. for 72 hours. Then, the cells were centrifuged at 9,300×g for two minutes and supernatant was collected. Next, the production level of MBL in the culture supernatant was determined.

Example 9

Determination of the MBL Production Levels by pZC1/hMBL, pZC5/hMBL, and pZC7/hMBL Transfected Clones The production level was assayed by ELISA. 96-well plates (F96 MAXI SORP Nunc-Immunoplate, Cat. no. 442404, Nunc) were coated with 1 µg/mL of anti-human MBL antibody (gift from Dr. Ohtani at Asahikawa Medical University, Japan) diluted with a coating buffer (15 mM $Na_2CO_3$, 35 mM $NaHCO_3$, 0.05% $NaN_3$, pH 9.6) at 4° C. for 16 hours. After blocking with 4% Block Ace (Dainippon Sumitomo Pharma Co., Ltd.), the 72-hour culture supernatant (1/1,000 to 1/100,000 dilution), two-fold dilution series (0.3125 to 20 ng/mL) of purified human MBL (gift from Dr. Ohtani at Asahikawa Medical University, Japan) in IS CHO-CD w/Hydrolysate medium (IS Japan) which is a serum-free medium for CHO cells, or IS CHO with Hydrolysate medium (IS Japan) was applied to the plates at 100 µL/well, and the plates were incubated at 37° C. for one hour. This was further incubated with 0.1 µg/mL of biotinylated human MBL monoclonal antibody (gift from Dr. Ohtani at Asahikawa Medical University, Japan) at 37° C. for one hour. VECTASTAIN Elite ABC Kit STANDARD (2 drops of Reagent A, 2 drops of Regent B/5 mL, Vector), which had been incubated at 37° C. for 30 minutes, was applied at 100 µL/well, and this was allowed to react at 37° C. for 45 minutes. PEROXIDASE SUBSTRATE KIT TMB (2 drops of Buffer, 3 drops of TMB, 2 drops of HYDROGEN PEROXIDE/5 mL, Vector), which had been incubated at room temperature for 30 minutes, was further applied at 100 µL/well, and after letting this react at room temperature for 15 minutes, 1 M phosphoric acid was added at 100 µL/well to stop the reaction. Protein concentration was determined using a microplate reader (Model 680, manufactured by BioRad). Results obtained by the ELISA method, and the top five samples showing high human MBL production levels are shown in Table 3. The clones with altered codon vectors show productivity equivalent to the vector with the unaltered codons.

TABLE 3

| hMBL production in Zeocin-resistant clone | |
|---|---|
| Clone name | Amount of production (µg/ml) |
| pZC1-23 | 11.7 |
| pZC1-26 | 8.8 |
| pZC1-27 | 14.3 |
| pZC1-30 | 15.1 |
| pZC1-46 | 12.4 |
| pZC5-1 | 12.2 |
| pZC5-3 | 7.7 |
| pZC5-12 | 7.0 |
| pZC5-39 | 8.3 |
| pZC5-44 | 8.2 |
| pZC7-4 | 7.9 |
| pZC7-5 | 9.1 |
| pZC7-6 | 8.5 |
| pZC7-9 | 10.1 |
| pZC7-38 | 8.8 |

Example 10 hMBL Production Levels by pZC1/hMBL, pZC5/hMBL, and pZC7/hMBL Transfected Cell Clones The distribution of hMBL expressed by the pZC1, pZC5, and pZC7 expression vectors of the present invention in each clone is shown in Table 4.

For pZC1, among the fifty Zeocin-resistant strains, 70.0% produced hMBL at 0 μg/mL or more to less than 5 μg/mL. Fifteen out of the fifty strains (30.0%) showed production levels of 5 μg/mL or more. Four out of the fifty strains (8.0%) showed production levels of 10 μg/mL or more. One out of the fifty strains (2.0%) showed production levels of 15 μg/mL or more. The strain showing the highest production level yielded 15.1 μg/mL in 3 days.

For pZC5, among the fifty Zeocin-resistant strains, 84.0% produced hMBL at 0 μg/mL or more to less than 5 μg/mL. Eight out of the fifty strains (16.0%) showed production levels of 5 μg/mL or more. One out of the fifty strains (2.0%) showed production levels of 10 μg/mL or more. The strain showing the highest production level yielded 12.2 μg/mL in 3 days.

For pZC7, among the forty-nine Zeocin-resistant strains, 75.5% produced hMBL at 0 μg/mL or more to less than 5 μg/mL. Twelve out of the forty-nine strains (24.5%) showed production levels of 5 μg/mL or more. One out of the forty-nine strains (2.0%) showed production levels of 10 μg/mL or more. The strain showing the highest production level yielded 10.1 μg/mL in 3 days.

Among pZCs, the production level of the clone showing the highest foreign protein production level was 15.1 μg/mL in 3 days; and among pNCs, the production level of the clone showing the highest foreign-protein production level was 46.1 μg/mL in 3 days. This showed that by altering codons of the drug resistance gene included as a component to the least frequently used codons, the foreign protein productivities of pNCs are significantly increased. Regarding pZCs, one can start the region of codon alteration of the drug resistance gene from the C-terminal side or central region of the sequence. Alternatively, one can think of alternately placing codons that will be altered and codons that will not be altered, and such. Either way, by adjusting the codons that will be altered, drug selection efficiency will increase, and such vectors are thought to be inserted into a position on the chromosome of the competent cells that has very high expression ability, as in the case with pNCs.

Example 11

Construction of pBC1 and pBC6

Figure 19:
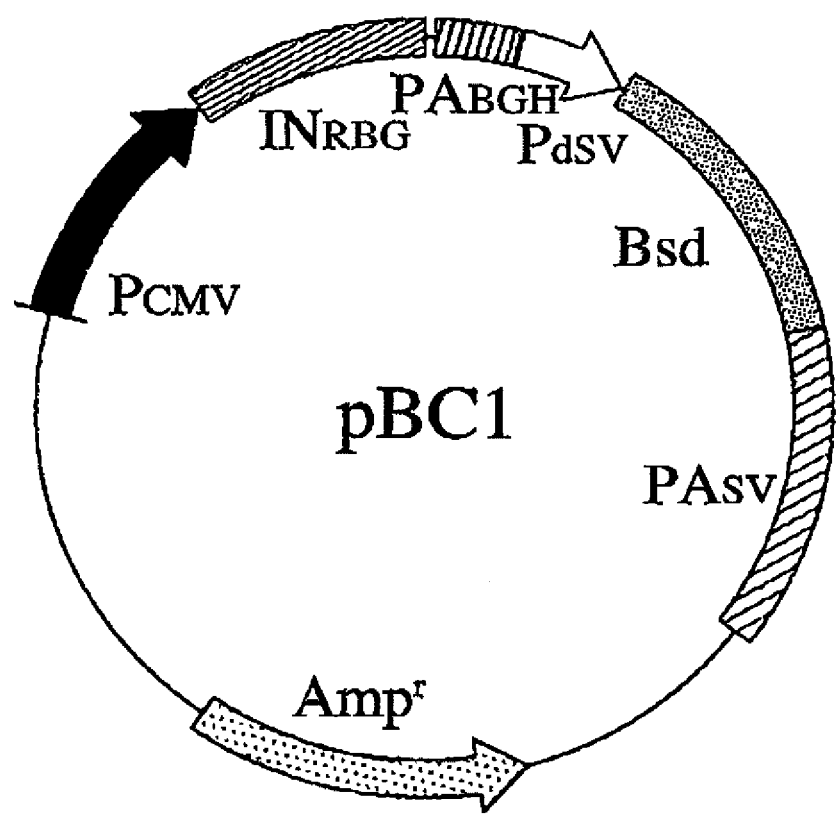
FIG. 19 shows the pBC1 construct. Each of the following indicates: PCMV: cytomegalovirus promoter; INRBG: rabbit growth hormone intron; PABGH: bovine growth hormone gene polyA additional signal; PdSV: enhancer-deleted simian virus 40 promoter; Bsd: blasticidin resistance gene (bsd gene) cDNA; PASV: simian virus 40 polyA additional signal; and Amp[r]: selection marker (ampicillin resistance) in E. coli.
Figure 20:
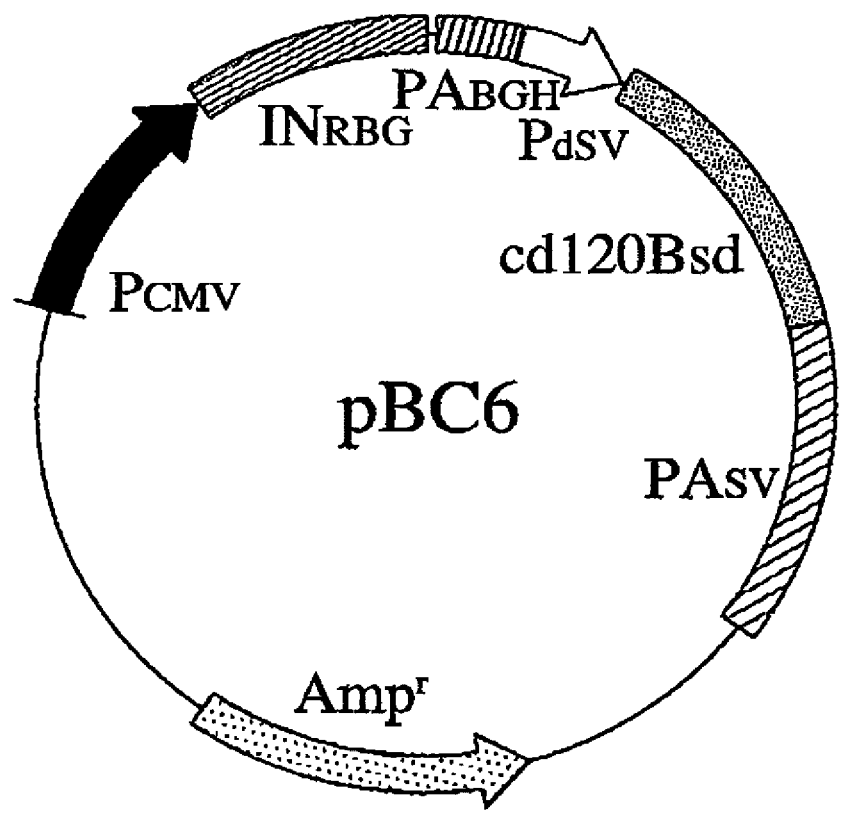
FIG. 20 shows the pBC6 construct. Each of the following indicates: PCMV: cytomegalovirus promoter; INRBG: rabbit growth hormone intron; PABGH: bovine growth hormone gene polyA additional signal; PdSV: enhancer-deleted simian virus 40 promoter; cd120Bsd: translation-impaired blasticidin resistance gene (bsd gene) produced by altering codons in the range of 120 bases from the 5' end of the nucleotide sequence of the blasticidin resistance gene to the least frequently used codons in mammals; PASV: simian virus 40 polyA additional signal; and Amp[r]: selection marker (ampicillin resistance) in E. coli.

Using methods well known to those skilled in the art, vectors of the present invention, pBC1 and pBC6, were constructed. pBC1 carries the wild-type blasticidin resistance gene (bsd gene) described in SEQ ID NO: 11 between nucleotides No. 1784 to No. 2578 in the sequence of backbone vector pNC1 (FIG. 19).

pBC6 is constructed by substituting nucleotides No. 1784 to No. 2578 in the sequence of pNC1 with the sequence of SEQ ID NO: 12. The substituted region of pBC6 is introduced with a translation-impaired blasticidin resistance gene in which codons in the range of 120 bases from the 5' end (30.1% codon alteration) of the nucleotide sequence of the blasticidin resistance gene have been altered to the least frequently used codons in mammals (FIG. 20).

Example 12

Construction of pBC1/hMBL and pBC6/hMBL

Figure 21:
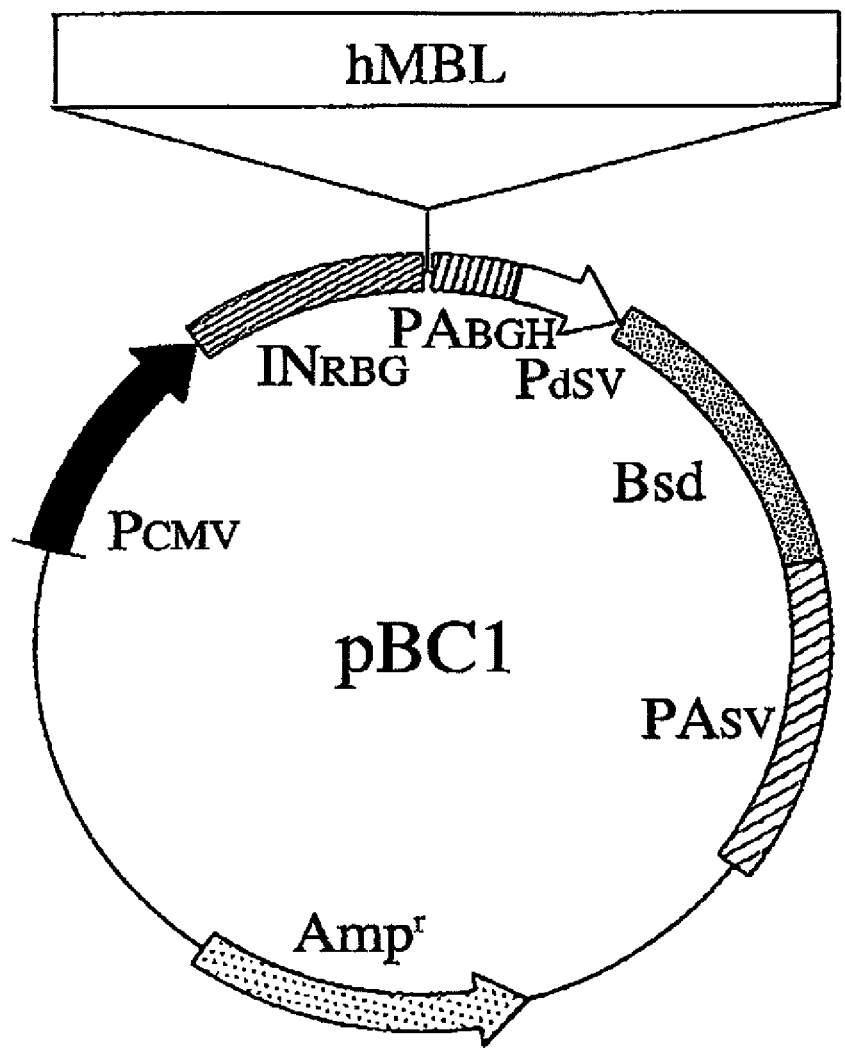
FIG. 21 shows the pBC1/hMBL construct. Each of the following indicates: PCMV: cytomegalovirus promoter; INRBG: rabbit growth hormone intron; hMBL: human mannose-binding lectin cDNA; PABGH: bovine growth hormone gene polyA additional signal; PdSV: enhancer-deleted simian virus 40 promoter; Bsd: blasticidin resistance gene (bsd gene) cDNA; PASV: simian virus 40 polyA additional signal; and Amp[r]: selection marker (ampicillin resistance) in E. coli.
Figure 22:
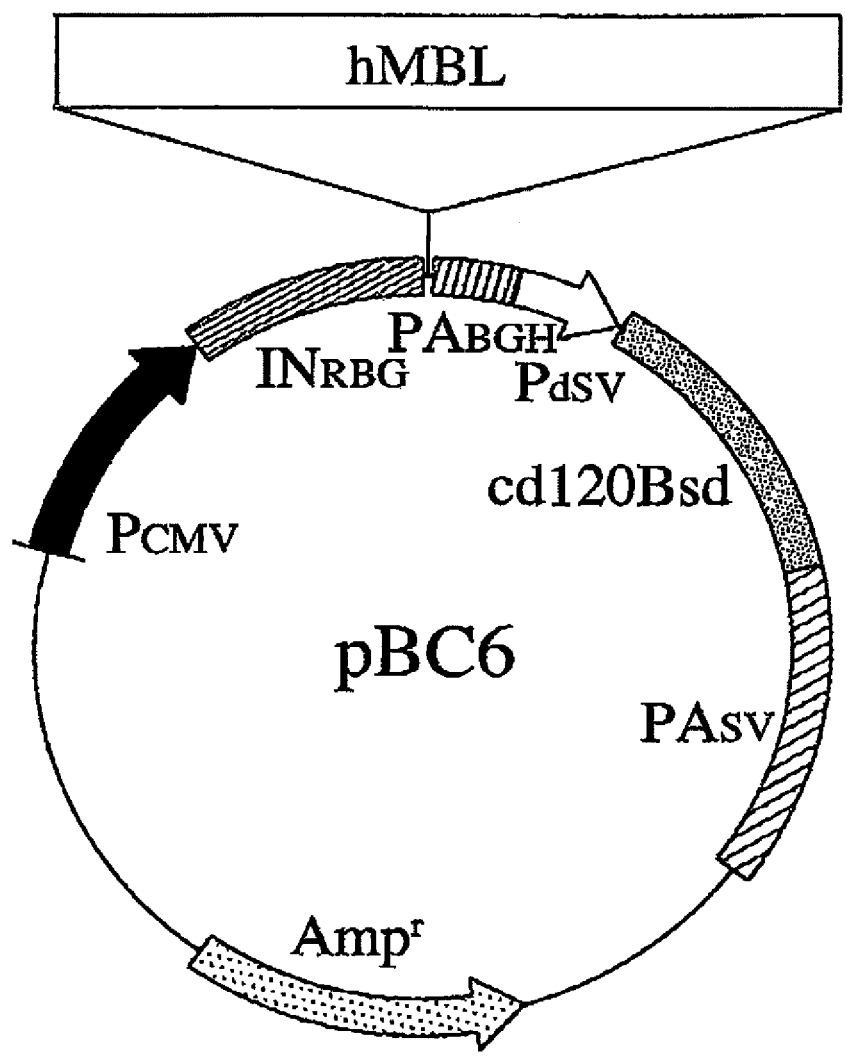
FIG. 22 shows the pBC6/hMBL construct. Each of the following indicates: PCMV: cytomegalovirus promoter; INRBG: rabbit growth hormone intron; hMBL: human mannose-binding lectin cDNA; PABGH: bovine growth hormone gene polyA additional signal; PdSV: enhancer-deleted simian virus 40 promoter; cd120Bsd: translation-impaired blasticidin resistance gene (bsd gene) produced by altering codons in the range of 120 bases from the 5' end of the nucleotide sequence of the blasticidin resistance gene to the least frequently used codons in mammals; PASV: simian virus 40 polyA additional signal; and Amp[r]: selection marker (ampicillin resistance) in E. coli.

Using methods well known to those skilled in the art, nucleotides No. 1267 to No. 1275 of vectors of the present invention, pBC1 and pBC6, were substituted with a cDNA encoding the human mannan-binding lectin (MBL) of SEQ ID NO: 6 (hereinafter referred to as hMBL), to construct pBC1/hMBL (FIG. 21) and pBC6/hMBL (FIG. 22).

Example 13

Transfection of pBC1/hMBL and pBC6/hMBL into CHO Cells, and Blasticidin Selection Using a CD Medium or a CD Medium Supplemented with Non-Animal-Based Additives 10 μg of pBC1/hMBL and pBC6/hMBL were transfected into $5.0 \times 10^5$ CHO cells (CHO DG44 cells) in 25 cm$^2$-culture flasks using the Lipofectin method (using Lipofectamine™ LTX; Invitrogen). Gene transfection was performed according to the manufacturer's instructions. 48 hours after gene transfection, the number of cells were counted, and then the cells were diluted in an IS CHO-CD w/Hydrolysate medium (IS Japan) supplemented with 4 mM Gluta MAX™-I (Invitrogen) and 10 μg/mL Blasticidin (Invitrogen). The cells were

TABLE 4

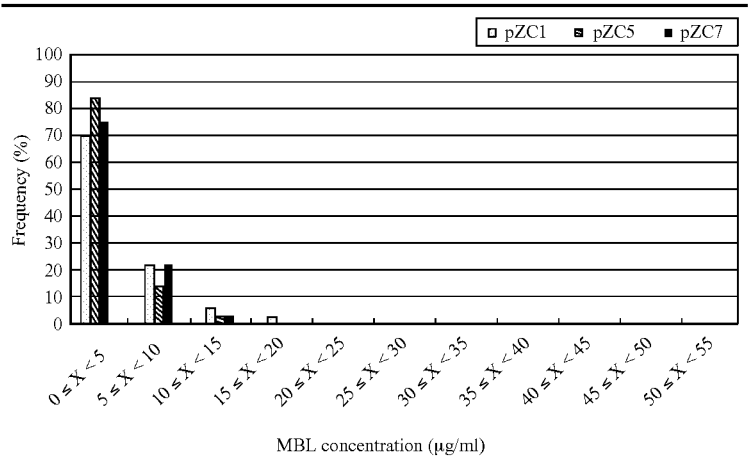

plated into five 96-well microtiter plates (480 wells) at a concentration of 4,000 cells/well, and after culturing in the presence of 5% carbon dioxide gas at 37° C. for approximately three weeks, surviving cells were observed (blasticidin-resistant clone). Blasticidin-resistant clones were arbitrarily selected from the surviving cells, transferred to 24-well plates together with the IS CHO-CD w/Hydrolysate medium (IS Japan) supplemented with 4 mM Gluta MAX™-I (Invitrogen) and 10 μg/mL Blasticidin (Invitrogen), and cultured until the cells occupied ⅓ or more of each well. 0.4 mL of each clone was placed into a sterile tube and centrifuged at 200×g for two minutes. The supernatant was discarded, and the cells were suspended in 0.1 mL of fresh medium (IS CHO-CD w/Hydrolysate medium (IS Japan) supplemented with 4 mM Gluta MAX™-I (Invitrogen)). After counting the number of cells, the cells were diluted with the medium to $5.0 \times 10^5$ cells/mL, then 0.2 mL of them were transferred to new 24-well plates, the cells were cultured in the presence of 5% carbon dioxide gas at 37° C. for 72 hours. Then, the cells were centrifuged at 9,300×g for two minutes and the supernatant was collected. Next, the production level of MBL in the culture supernatant was determined.

Example 14

Determination of the MBL Production Level by pBC1/hMBL and pBC6/hMBL Transfected Clones The production level was assayed by ELISA. 96-well plates (F96 MAXI SORP Nunc-Immunoplate, Cat. no. 442404, Nunc) were coated with 1 μg/mL of anti-human MBL antibody (gift from Dr. Ohtani at Asahikawa Medical University, Japan) diluted with a coating buffer (15 mM $Na_2CO_3$, 35 mM $NaHCO_3$, 0.05% $NaN_3$, pH 9.6) at 4° C. for 16 hours. After blocking with 4% Block Ace (Dainippon Sumitomo Pharma Co., Ltd.), the 72-hour culture supernatant (1/1,000 to 1/100,000 dilution), two-fold dilution series (0.3125 to 20 ng/mL) of purified human MBL (gift from Dr. Ohtani at Asahikawa Medical University, Japan) in IS CHO-CD w/Hydrolysate medium (IS Japan) which is a serum-free medium for CHO cells, or IS CHO with Hydrolysate medium (IS Japan) was applied to the plates at 100 μL/well and the plates were incubated at 37° C. for one hour. This was further incubated with 0.1 μg/mL of biotinylated human MBL monoclonal antibody (gift from Dr. Ohtani at Asahikawa Medical University, Japan) at 37° C. for one hour. VECTASTAIN Elite ABC Kit STANDARD (2 drops of Reagent A, 2 drops of Regent B/5 mL, Vector), which had been incubated at 37° C. for 30 minutes, was applied at 100 μL/well, and this was allowed to react at 37° C. for 45 minutes. PEROXIDASE SUBSTRATE KIT TMB (2 drops of Buffer, 3 drops of TMB, 2 drops of HYDROGEN PEROXIDE/5 mL, Vector), which had been incubated at room temperature for 30 minutes, was further applied at 100 μL/well, and after letting this react at room temperature for 15 minutes, 1 M phosphoric acid was added at 100 μL/well to stop the reaction. Protein concentration was determined using a microplate reader (Model 680, manufactured by BioRad). Results obtained by the ELISA method, and the top five samples showing high human MBL production levels are shown in Table 5. The clones with altered codon vectors show productivity equivalent to the vector with the unaltered codons.

TABLE 5 hMBL production in Blasticidin-resistant clone

| Clone name | Amount of production (μg/ml) |
| --- | --- |
| pBC1-6 | 6.2 |
| pBC1-19 | 11.2 |
| pBC1-22 | 9.2 |
| pBC1-35 | 7.5 |
| pBC1-48 | 5.7 |
| pBC6-13 | 7.9 |
| pBC6-19 | 9.1 |
| pBC6-25 | 11.5 |
| pBC6-32 | 8.5 |
| pBC6-45 | 12.5 |

Example 15 hMBL Production Levels by pBC1/hMBL and pBC6/hMBL Transfected Cell Clones

The distribution of hMBL expressed by the pBC1 and pBC6 expression vectors of the present invention in each clone is shown in Table 6.

For pBC1, among the fifty-six Blasticidin-resistant strains, 83.9% produced hMBL at 0 μg/mL or more to less than 5 μg/mL. Nine out of the fifty-six strains (26.1%) showed production levels of 5 μg/mL or more. One out of the fifty-six strains (1.8%) showed production levels of 10 μg/mL or more. The strain showing the highest production level yielded 11.2 μg/mL in 3 days.

For pBC6, among the fifty-nine Blasticidin-resistant strains, 66.1% produced hMBL at 0 μg/mL or more to less than 5 μg/mL. Twenty out of the fifty-nine strains (33.9%) showed production levels of 5 μg/mL or more. Three out of the fifty-nine strains (5.1%) showed production levels of 10 μg/mL or more. The strain showing the highest production level yielded 12.5 μg/mL in 3 days.

Among pBCs, the production level of the clone showing the highest foreign protein production level was 12.5 μg/mL in 3 days; and among pNCs, the production level of the clone showing the highest foreign-protein production level was 46.1 μg/mL/3 days. This showed that by altering the codons of the drug resistance gene included as a component to the least frequently used codons, the foreign protein productivities of pNCs are significantly increased. Regarding pBCs, one can start the region of codon alteration of the drug resistance gene from the C-terminal side or central region of the sequence. Alternatively, one can think of alternatively placing codons that will be altered and codons that will not be altered, and such. Either way, by adjusting the codons that will be altered, drug selection efficiency will increase, and such vectors are thought to be inserted into a position on the chromosome of the competent cells that has very high expression ability, as in the case with pNCs.

TABLE 6

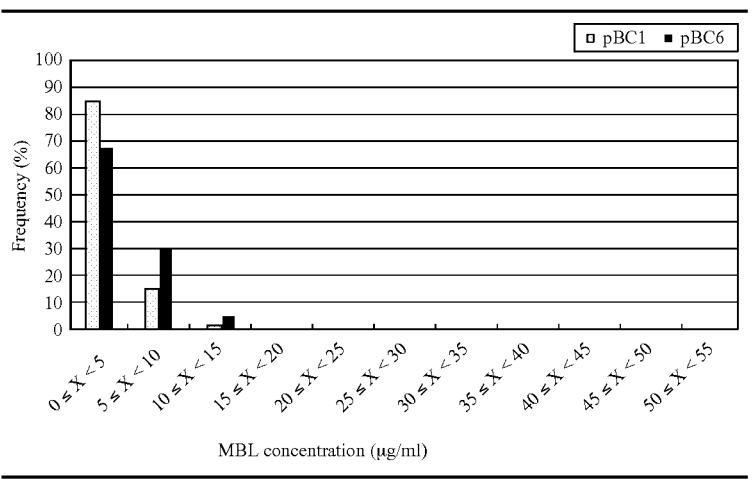

MBL concentration (μg/ml)

INDUSTRIAL APPLICABILITY

The present invention can provide expression vectors that enable high-level production of foreign gene-derived proteins using mammalian cells as host. Furthermore, they can produce proteins that have post-translational modifications inherent to mammals and high biological activity. Therefore, the production cost of useful protein substances such as biopharmaceuticals can be significantly reduced.

Furthermore, since the methods for protein production according to the present invention do not use viruses or microorganisms, highly safe protein production is possible.

The invention claimed is:

1. An expression vector for producing a foreign gene-derived protein in a mammalian host cell, which comprises:
   (a) a translation-impaired drug resistance gene cassette comprising a region with rare codons
      wherein the rare codons comprise GCA for alanine, CGA for arginine, AAU for asparagine, GAU for aspartic acid, UGU for cysteine, CAA for glutamine, GAA for glutamic acid, GGU for glycine, CAU for histidine, UUA for leucine, AAA for lysine, CCA for proline, UUU for phenylalanine, UCA for serine, ACU for threonine, UAU for tyrosine, and GUA for valine,
      wherein from the 5' end of the drug resistance gene, each of at least the first 30% of the drug resistance gene codons is replaced by the rare codon encoding the same amino acid as the drug resistance gene codon,
      wherein the translation-impaired drug resistance gene cassette uses a promoter whose enhancer portion has been removed, and wherein the drug resistance gene is a neomycin phosphotransferase gene (NTP gene); and
   (b) a gene cassette comprising a cloning site for integration of a foreign gene between a transcriptionally active promoter and a stable polyadenylation signal.

2. A method for producing a transformant that has ability to produce a high level of a foreign gene-derived protein and to resist neomycin; which comprises the steps of inserting a foreign gene into the expression vector of claim 1, and transforming a host cell using the expression vector.

3. A method for producing a foreign gene-derived protein, which comprises the steps of:
   (a) inserting a foreign gene into the expression vector of claim 1;
   (b) transforming a host cell with the expression vector;
   (c) culturing the transformant in a medium supplemented with neomycin; and
   (d) collecting the foreign gene-derived protein from the cultured transformant.

4. The production method of claim 3, wherein a chemically defined medium (CD medium) or a medium supplemented with a non-animal-based additive to the CD medium is used for culturing in step (c) of claim 3.

5. An expression vector for producing a foreign gene-derived protein in a mammalian host cell, which comprises:
   (a) a translation-impaired drug resistance gene cassette comprising a region with rare codons
      wherein the rare codons comprise GCA for alanine, CGA for arginine, AAU for asparagine, GAU for aspartic acid, UGU for cysteine, CAA for glutamine, GAA for glutamic acid, GGU for glycine, CAU for histidine, UUA for leucine, AAA for lysine, CCA for proline, UUU for phenylalanine, UCA for serine, ACU for threonine, UAU for tyrosine, and GUA for valine,
      wherein from the 5' end of the drug resistance gene, each of at least the first 30% of the drug resistance gene codons is replaced by the rare codon encoding the same amino acid as the drug resistance gene codon,
      wherein the translation-impaired drug resistance gene cassette uses a promoter whose enhancer portion has been removed, and wherein the drug resistance gene is a blasticidin resistance gene (Blasticidin gene); and
   (b) a gene cassette comprising a cloning site for integration of a foreign gene between a transcriptionally active promoter and a stable polyadenylation signal.

6. A method for producing a transformant that has ability to produce a high level of a foreign gene-derived protein and to resist blasticidin; which comprises the steps of inserting a foreign gene into the expression vector of claim 5, and transforming a host cell using the expression vector.

7. A method for producing a foreign gene-derived protein, which comprises the steps of:
   (a) inserting a foreign gene into the expression vector of claim 5;
   (b) transforming a host cell with the expression vector;
   (c) culturing the transformant in a medium supplemented with blasticidin; and
   (d) collecting the foreign gene-derived protein from the cultured transformant.

8. The production method of claim 7, wherein a chemically defined medium (CD medium) or a medium supplemented with a non-animal-based additive to the CD medium is used for culturing in step (c) of claim 7.

* * * * *